(12) United States Patent
Bonnert et al.

(10) Patent No.: US 7,166,607 B2
(45) Date of Patent: Jan. 23, 2007

(54) SUBSTITUTED INDOLES

(75) Inventors: Roger Bonnert, Leicestershire (GB); Stephen Brough, Leicestershire (GB); Tony Cook, Leicestershire (GB); Mark Dickinson, Leicestershire (GB); Rukhsana Rasul, Leicestershire (GB); Hitesh Sanganee, Leicestershire (GB); Simon Teague, Leicestershire (GB)

(73) Assignee: AstraZeneca AB (SE)

( * ) Notice: Subject to any disclaimer, the term of this patent is extended or adjusted under 35 U.S.C. 154(b) by 31 days.

(21) Appl. No.: 10/516,557

(22) PCT Filed: May 27, 2003

(86) PCT No.: PCT/SE03/00856

§ 371 (c)(1),
(2), (4) Date: Nov. 30, 2004

(87) PCT Pub. No.: WO03/001961

PCT Pub. Date: Dec. 11, 2003

(65) Prior Publication Data

US 2005/0165055 A1    Jul. 28, 2005

(30) Foreign Application Priority Data

May 30, 2002  (SE) .................... 0201635

(51) Int. Cl.
*A61K 31/496*  (2006.01)
*A61K 31/4196*  (2006.01)
*A61K 31/422*  (2006.01)
*A61K 31/4709*  (2006.01)
*A61K 31/426*  (2006.01)
*C07D 403/04*  (2006.01)
*C07D 403/12*  (2006.01)

(52) U.S. Cl. ............ 514/254.01; 514/397; 514/384; 514/376; 514/307; 514/369; 548/312.1; 548/264.4; 548/229; 548/187; 544/238; 546/148

(58) Field of Classification Search ............. 544/238; 514/254.01, 397, 384, 376, 307, 369; 548/312.1, 548/264.4, 229, 187; 546/148
See application file for complete search history.

(56) References Cited

U.S. PATENT DOCUMENTS

| 5,459,150 A | 10/1995 | Brooks et al. |
| 5,486,525 A | 1/1996 | Summers, Jr. et al. |
| 5,567,711 A | 10/1996 | Sheppard et al. |
| 2005/0222201 A1 | 10/2005 | Birkinshaw et al. |

FOREIGN PATENT DOCUMENTS

| EP | 0 530 907 A1 | 3/1993 |
| EP | 0 576 347 A1 | 12/1993 |
| EP | 0924209 B1 | 6/1999 |
| EP | 1 170 594 A2 | 1/2002 |
| EP | 1505061 | 2/2005 |
| GB | 1356834 | 6/1974 |
| WO | WO 94/19321 | 9/1994 |
| WO | WO 94/16687 | 6/1995 |
| WO | WO98/13368 | 4/1998 |
| WO | WO99/09007 | 2/1999 |
| WO | WO00/78761 | 12/2000 |
| WO | WO01/47922 | 7/2001 |
| WO | WO01/92224 | 12/2001 |
| WO | WO03/064387 | 8/2003 |
| WO | WO03/101961 | 12/2003 |
| WO | WO03/101981 A1 | 12/2003 |
| WO | WO2004/007451 A1 | 1/2004 |
| WO | WO2004/106302 A1 | 12/2004 |
| WO | WO2005/019171 A1 | 3/2005 |
| WO | WO2005/054232 A1 | 6/2005 |

OTHER PUBLICATIONS

Luscher et al., "Deblocking of o-Nitrophenylsufenyl-Protected Peptides by Ammonium Thiocyanate and (2-Methyl-1-indolyl)acetic acid", Helv. Chim. Acta 66(2):602-605 (1983).*
Atkinson et al., "A New Synthesis of 3-Arylthioindoles", *Synthesis* 6:480-481 (1988).
Garcia et al., "A Novel Synthesis of 3-Cyanoindoles and a New Route to Indole-3-Carboxylic Acid Derivatives", *Tetrahedron Letters* 26(15):1827-1830 (1985).
Hamel et al., "Regioselective Synthesis of Mixed Indole 2,3-Bis(sulfides). A Study of the Mechanism of the Second Sulfenylation of Indole", *J. Org. Chem.* 61:1573-1577 (1996).
Hary et al., "Efficient synthesis of 3-(4,5-dihydro-1H-imidazole-2-yl)-1H-indoles", *Tetrahedron Letters* 42:5187-5189 (2001).
Lüscher et al., "Deblocking of o-Nitrophenylsulfenyl-Protected Peptides by Ammonium Thiocyanate and (2-Methyl-1-indolyl) acetic acid", *Helv. Chim. Acta* 66(2):602-605 (1983).

(Continued)

*Primary Examiner*—Joseph K. McKane
*Assistant Examiner*—Michael Barker
(74) *Attorney, Agent, or Firm*—Fish & Richardson P.C.

(57) ABSTRACT

The present invention relates to substituted indoles of formula (I) useful as pharmaceutical compounds for treating respiratory disorders

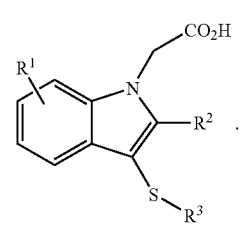

(I)

7 Claims, No Drawings

OTHER PUBLICATIONS

Matsugi et al., "An efficient sylfenylation of aromatics using highly active quinone mono O,S-acetal bearing a pentafluorophenylthio group", *Tetrahedron Letters* 42:1077-1080 (2001).

Matsugi et al., "Facile and Efficient Sulfenylation Method Using Quinone Mono-O,S-Acetals under Mild Conditions", *J. Org. Chem.* 66:2434-2441 (2001).

STN International, CAPLUS accession No. 1977:535057, Document No. 87:135057, Sankyo Co., Ltd., "3-Indolyl thio ethers", & JP,A2,52039671, 19770328, RN 64137-76-4, 54491-43-9, 56366-45-1.

STN International, CAPLUS accession No. 2001:338492, Document No. 134:353315, Wakunaga Pharmaceutical Co., Ltd., "Preparation of indole derivatives as chymase inhibitors and drugs containing the same as the active ingredient", & WO,A1,2001032621, 20010510, RN 64137-76-4, 336186-33-5.

STN International, CHEMCATS accession No. 2000:1027702, Apr. 26, 2001, 8004-3013, "1H-Indole-1-acetic acid, 2-methyl-3-(phenylthio)-, ethyl ester", CAS Registry No. 300860-50-8.

Database CA 'Online! Chemical Abstracts Service, Columbus, Ohio, US; Tanimoto, Norihiko et al: "Preparation of indole derivatives as PGD2 receptor antagonists" XP002301963 retrieved from STN Database accession No. 2003:931327.

Ovenden et al., "Echinosulfonic Acids A-C and Echinosulfone A: Novel Bromoindole Sulfonic Acids and a Sulfone from a Southern Australian Marine Sponge, *Echinodictyum*", *J. Nat. Prod.* 62:1246-1249 (1999).

STN International, CAPLUS accession No. 1980:6356, Document No. 92:6356, Gabrielyan, G.E. et al.: "Indole derivatives. LX. Synthesis of indole compounds with a furan ring", & Armyanskii Khimicheskii Zhurnal (1979), 32(4), 309-14, RN 51842-57-0.

STN International, CAPLUS accession No. 2001:235566, Document No. 134:266203, Kato, Susumu et al.: "Preparation and application of benzopyranone derivatives"; & JP,A2,2001089471, 20010403, RN 332082-10-7.

* cited by examiner

SUBSTITUTED INDOLES

CROSS-REFERENCE TO RELATED APPLICATIONS

This application is the national phase application under 35 U.S.C. § 371 of PCT International Application No. PCT/SE03/00856, filed May 27, 2003, which claims priority to Swedish Application Serial No. 0201635-0, filed May 30, 2002.

The present invention relates to substituted indoles useful as pharmaceutical compounds for treating respiratory disorders, pharmaceutical compositions containing them, and processes for their preparation.

EPA 1 170 594 discloses methods for the identification of compounds useful for the treatment of disease states mediated by prostaglandin D2, a ligand for orphan receptor CRTh2. GB 1356834 discloses a series of compounds said to possess anti-inflammatory, analgesic and antipyretic activity. It has now surprisingly been found that certain indole acetic acids are active at the CRTh2 receptor, and as a consequence are expected to be potentially useful for the treatment of various respiratory diseases, including asthma and COPD.

In a first aspect the invention therefore provides a compound of formula (I) or a pharmaceutically acceptable salt or solvate thereof:

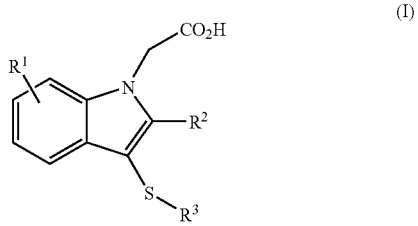

in which $R^1$ is hydrogen, halogen, CN, nitro, $SO_2R^4$, OH, $OR^4$, $S(O)xR^4$, $SO_2NR^5R^6$, $CONR^5R^6$, $NR^5R^6$, aryl (optionally substituted by chlorine or fluorine), $C_2$–$C_6$ alkenyl, $C_2$–$C_6$ alkynyl or $C_{1-6}$ alkyl, the latter three groups being optionally substituted by one or more substituents independently selected from halogen, $OR^8$ and $NR^5R^6$, $S(O)_xR^7$ where x is 0, 1 or 2;

$R^2$ is hydrogen, halogen, CN, $SO_2R^4$ or $CONR^5R^6$, $CH_2OH$, $CH_2OR^4$ or $C_{1-7}$alkyl, the latter group being optionally substituted by one or more substituents independently selected from halogen atoms, $OR^8$ and $NR^5R^6$, $S(O)_xR^7$ where x is 0, 1 or 2;

$R^3$ is aryl or heteroaryl each of which is optionally substituted by one or more substituents independently selected from hydrogen, halogen, CN, nitro, OH, $SO_2R^4$, $OR^4$, $SR^4$, $SOR^4$, $SO_2NR^5R^6$, $CONR^5R^6$, $NR^5R^6$, $NHCOR^4$, $NHSO_2R^4$, $NHCO_2R^4$, $NR^7SO_2R^4$, $NR^7CO_2R^4$, $C_2$–$C_6$ alkenyl, $C_2$–$C_6$ alkynyl, $C_{1-6}$ alkyl, the latter three groups being optionally substituted by one or more substituents independently selected from halogen atoms, $OR^8$ and $NR^5R^6$, $S(O)_xR^7$ where x=0, 1 or 2;

$R^4$ represents aryl, heteroaryl, or $C_{1-6}$alkyl all of which may be optionally substituted by one or more substituents independently selected from halogen atoms, aryl, heteroaryl, $OR^{10}$, OH, $NR^{11}R^{12}$, $S(O)_xR^{13}$ (where x=0, 1 or 2), $CONR^{14}R^{15}$, $NR^{14}COR^{15}$, $SO_2NR^{14}R^{15}$, $NR^{14}SO_2R^{15}$, CN, nitro;

$R^5$ and $R^6$ independently represent a hydrogen atom, a $C_{1-6}$alkyl group, or an aryl, or a heteroaryl, the latter three of which may be optionally substituted by one or more substituents independently selected from halogen atoms, aryl, $OR^8$ and $NR^{14}R^{15}$, $CONR^{14}R^{15}$, $NR^{14}COR^{15}$, $SO_2NR^{14}R^{15}$, $NR^{14}SO_2R^{15}$; CN, nitro or $R^5$ and $R^6$ together with the nitrogen atom to which they are attached can form a 3–8 membered saturated heterocylic ring optionally containing one or more atoms selected from O, $S(O)_x$ where x=0, 1 or 2, $NR^{16}$, and itself optionally substituted by $C_{1-3}$ alkyl;

$R^7$ and $R^{13}$ independently represent a $C_1$–$C_6$, alkyl, an aryl or a heteroaryl group, all of which may be optionally substituted by halogen atoms;

$R^8$ represents a hydrogen atom, $C(O)R^9$, $C_1$–$C_6$ alkyl (optionally substituted by halogen atoms or aryl) an aryl or a heteroaryl group (optionally substituted by halogen);

each of $R^9$ $R^{10}$, $R^{11}$, $R^{12}$, $R^{14}$, $R^{15}$, independently represents a hydrogen atom, $C_1$–$C_6$ alkyl, an aryl or a heteroaryl group (all of which may be optionally substituted by halogen atoms); and $R^{16}$ is hydrogen, $C_{1-4}$ alkyl, —$COC_1$–$C_4$ alkyl, $COYC_1$–$C_4$alkyl where Y is O or $NR^7$, provided that when $R^1$ is hydrogen and $R^2$ is methyl, then $R^3$ is not 2-nitrophenyl.

In the context of the present specification, unless otherwise indicated, an alkyl or alkenyl group or an alkyl or alkenyl moiety in a substituent group may be linear, branched or cylclic.

Aryl is phenyl or naphthyl.

Heteroaryl is defined as a 5–7 membered aromatic ring or can be 6,6- or 6,5-fused bicyclic each ring containing one or more heteroatoms selected from N, S and O. Examples include pyridine, pyrimidine, thiazole, oxazole, pyrazole, imidazole, furan, isoxazole, pyrrole, isothiazole and azulene, naphthyl, indene, quinoline, isoquinoline, indole, indolizine, benzo[b]furan, benzo[b]thiophene, 1H-indazole, benzimidazole, benzthiazole, 1,2benzisothiazole, benzoxazole, purine, 4H-quinolizine, cinnoline, phthalazine, quinazoline, quinoxaline, 1,8-naphthyridine, pteridine, quinolone.

Heterocyclic rings as defined for $R^5$ and $R^6$ means saturated heterocycles, examples include morpholine, thiomorpholine, azetidine, imidazolidine, pyrrolidine, piperidine and piperazine.

The term alkyl, whether alone or as part of another group, includes straight chain, branched or cyclic alkyl groups.

Preferably $R^1$ is hydrogen, halogen, nitro, $NR^4R^5$, nitrile, $SO_2R^4$, $SO_2NR^5R^6$, OMe, aryl, $CO_2R^8$ or $C_{1-6}$ alkyl which may be optionally substituted by one or more substituents independently selected from halogen atoms, $OR^8$ and $NR^8R^9$, $S(O)_xR^7$ where x=0, 1 or 2. More than one $R^1$ substituent can be present and these can be the same or different. More preferably $R^1$ is aryl, hydrogen, methyl, chloro, fluoro, nitrile, nitro, bromo, iodo, $SO_2Me$, $SO_2Et$, $NR^4R^5$, $SO_2N$-alkyl$_2$, alkyl (optionally substituted by fluorine atoms) Most preferably $R^1$ is hydrogen, methyl, phenyl, chloro, fluoro, iodo, nitrile, $SO_2Me$, $CF_3$, nitrile.

The $R^1$ group or groups can be present at any suitable position on the indole ring, preferably the $R^1$ group(s) are (is) at the 4 and (or) 5-position. Preferably the number of substiutents $R^1$ other than hydrogen is 1 or 2.

Preferably $R^2$ is $C_{1-6}$alkyl, more preferably methyl.

Suitably $R^3$ is phenyl or heteroaryl. Suitable heteroaryl groups includes a 6,6- or 6,5-fused bicyclic aromatic ring systems optionally containing one to three heteroatoms selected from nitrogen, oxygen or sulphur, or a 5- to 7-membered heterocyclic ring containing one to three heteroatoms selected from nitrogen, oxygen or sulphur.

Examples of suitable heteroaryl groups include pyridine, pyrimidine, thiazole, oxazole, pyrazole, imidazole, furan, isoxazole, pyrrole, isothiazole and azulene, naphthyl, indene, quinoline, isoquinoline, indole, indolizine, benzo[b]furan, benzo[b]thiophene, 1H-indazole, benzimidazole, benzthiazole, benzoxazole, purine, 4H-quinolizine, cinnoline, phthalazine, quinazoline, quinoxaline, 1,8-naphthyridine, pteridine, indole, 1,2-benzisothiazole and quinolone.

Preferably $R^3$ is quinolyl, phenyl or thiazole, each of which can be substituted as defined above. More preferably $R^3$ is phenyl or quinolyl, each of which can be substituted as defined above.

The $R^3$ group may be substituted by one or more substituents from halogen, methoxy, alkyl, $CF_3$, $SO_2$alkyl, aryl or cyano. More preferably the substituents on $R^3$ are fluorine, chlorine, methyl, ethyl, isopropyl, methoxy, $SO_2Me$, trifluoromethyl or aryl. Preferably, substituents can be present on any suitable position of an $R^3$ group. Most preferably when $R^3$ is phenyl the substituents are present at the 4-position.

When $R^3$ is a heterocycle, heteroatom(s) can be present at any position in the ring.

Preferred compounds of the invention include:
3-[(4-chlorophenyl)thio]-2,5-dimethyl-1H-indol-1-acetic acid;
3-[(2-chloro-4-fluorophenyl)thio]-2,5-dimethyl-1H-indol-1-acetic acid;
3-[(3-chlorofluorophenyl)thio]-2,5-dimethyl-1H-indol-1-acetic acid;
3-[(2-methoxyphenyl)thio]-2,5-dimethyl-1H-indol-1-acetic acid;
3-[(3-fluorophenyl)thio]-2,5-dimethyl-1H-indol-1-acetic acid;
3-[(4-ethylphenyl)thio]-2,5-dimethyl-1H-indol-1-acetic acid;
3-[(2-chlorophenyl)thio]-2,5-dimethyl-1H-indol-1-acetic acid;
3-[(2,5-chlorophenyl)thio]-2,5-diethyl-1H-indol-1-acetic acid;
3-[(4-fluorophenyl)thio]-2,5-dimethyl-1H-indol-1-acetic acid;
3-[(4-chloro-2-methylphenyl)thio]-2,5-dimethyl-1H-indol-1-acetic acid;
3-[(4-chlorophenyl)thio]-4-cyano-2,5-dimethyl-1H-indole-1-acetic acid;
5-chloro-3-[(4-chlorophenyl)thio]-6-cyano-2-methyl-1H-indole-1-acetic acid;
3-[(4-chlorophenyl)thio]4-(ethylsulfonyl)-7-methoxy-2-methyl-1H-indole-1-acetic acid;
3-[(4-chlorophenyl)thio]4-[(diethylamino)sulfonyl]-7-methoxy-2-methyl-1H-indole-1-acetic acid;
4-chloro-3-[(4-chlorophenyl)thio]-2-methyl-1H-indole-1-acetic acid;
5-chloro-3-[(4-chlorophenyl)thio]-2-methyl-1H-indole-1-acetic acid;
6-chloro-3-[(4-chlorophenyl)thio]-2-methyl-1H-indole-1-acetic acid;
7-chloro-3-[(4-chlorophenyl)thio]-2-methyl-1H-indole-1-acetic acid;
3-[(4-chlorophenyl)thio]-2-methyl-5-methylsulfonyl)-1H-indole-1-acetic acid;
2-methyl-3-[(4-methylphenyl)thio]-6-(methylsulfonyl)-1H-indole-1-acetic acid;
4-bromo-3-[(4-chlorophenyl)thio]-2-methyl-1H-indole-1-acetic acid;
3-[(4-chlorophenyl)thio])-4-[4-[(1,1-dimethylethoxy)carbonyl]-1-piperazinyl]-2-methyl-1H-indole-1-acetic acid;
3-[(4-chlorophenyl)thio]-2-methyl-4-(1-piperazinyl)-1H-indole-1-acetic acid;
5-bromo-3-[(4-chlorophenyl)thio]-2-methyl-1H-indole-1-acetic acid;
3-[(4-chlorophenyl)thio]-2-methyl-5-phenyl-1H-indole-1-acetic acid;
3-[(4-chlorophenyl)thio]-5-cyano-2-methyl-1H-indole-1-acetic acid;
3-[(4-cyanophenyl)thio]-2,5-dimethyl-1H-indol-1-acetic acid,
3-[(3-methoxyphenyl)thio]-2,5-dimethyl-1H-indole-1-acetic acid;
3-[(4-methoxyphenyl)thio]-2,5-dimethyl-1H-indole-1-acetic acid,
3-[(3-ethylphenyl)thio]-2,5-dimethyl-1H-indole-1-acetic acid;
2,5-dimethyl-3-[(2-methylphenyl)thio]-1H-indole-1-acetic acid;
3-[(3-chlorophenyl)thio]-2,5-dimethyl-1H-indole-1-acetic acid,
3-[(2-Fluorophenyl)thio]-2,5-dimethyl-1H-indole-1-acetic acid,
3-[(2,6-Dichlorophenyl)thio]-2,5 dimethyl-1H-indole-1-acetic acid;
3-(1H-Imidazol-2-ylthio)-2,5-dimethyl-1H-indole-1-acetic acid,
2,5-Dimethyl-3-(1H-1,2,4-triazol-3-ylthio)-1H-indole-1-acetic acid;
2,5-Dimethyl-3-[(4-methyl-4H-1,2,4-triazol-3-yl)thio]-1H-indole-1-acetic acid;
2,5-Dimethyl-3-[(4-methyl-2-oxazolyl)thio]-1H-indole-1-acetic acid;
2,5-Dimethyl-3-[(1-methyl-1H-imidazol-2-yl)thio]-1H-indole-1-acetic acid;
2,5-Dimethyl-3-[[4-(methylsulfonyl)phenyl]thio]-1H-indole-1-acetic acid,
2,5-Dimethyl-3-(8-quinolinylthio)-1H-indole-1-acetic acid,
3-[(4-Chlorophenyl)thio]-5-fluoro-2,4-dimethyl-1H-indole-1-acetic acid;
3-[(4-Cyanophenyl)thio]-5-fluoro-2,4-dimethyl-1H-indole-1-acetic acid;
3-[(2-Chlorophenyl)thio]-5-fluoro-2,4-dimethyl-1H-indole-1-acetic acid;
5-Fluoro-3-[(2-methoxyphenyl)thio]-2,4-dimethyl-1H-indole-1-acetic acid;
5-Fluoro-3-[(2-ethylphenyl)thio]-2,4-dimethyl-1H-indole-1-acetic acid;
5-Fluoro-2,4 diethyl-3-[[2-(1-methylethyl)phenyl]thio]-1H-indole-1-acetic acid;
5-fluoro-2,4-dimethyl-3-[[2-(trifluoromethyl)phenyl]thio]-1H-indole-1-acetic acid;
2,5-dimethyl-4-(methylsulfonyl)-3-[(4-phenyl-2-thiazolyl)thio]-1H-indole-1-acetic acid;
3-[(3-chlorophenyl)thio]-2,5-dimethyl-4-(methylsulfonyl)-1H-indole-1-acetic acid;
3-[(2-chlorophenyl)thio]-2,5-dimethyl-4-(methylsulfonyl)-1H-indole-1-acetic acid;
3-[(4-chlorophenyl)thio]-5-methoxycarbonyl)-2-methyl-1H-indole-1-acetic acid;
5-carboxy-3-[(4-chlorophenyl)thio]-2-methyl-1H-indole-1-acetic acid;
3-[(4-chlorophenyl)thio]-2-methyl-4-nitro-1H-indole-1-acetic acid;

4-amino-3-[(4-chlorophenyl)thio]-2-methyl-1H-indole-1-acetic acid;
3-[(4-chlorophenyl)thio]-4-(ethylamino)-2-methyl-1H-indole-1-acetic acid;
3-[(4-chlorophenyl)thio]-4-iodo-2-methyl-1H-indole-1-acetic acid;
3-[(4-chlorophenyl)thio]-2-methyl-4-phenyl-1H-indole-1-acetic acid;

and pharmaceutically acceptable salts thereof.

Certain compounds of formula (I) are capable of existing in stereo isomeric forms. It will be understood that the invention encompasses all geometric and optical isomers of the compounds of formula (I) and mixtures thereof including racemates. Tautomers and mixtures thereof also form an aspect of the present invention.

The compound of formula (I) above may be converted to a pharmaceutically acceptable salt or solvate thereof, preferably a basic addition salt such as ammonium, sodium, potassium, calcium, aluminium, lithium, magnesium, zinc, benzathine, chloroprocaine, choline, diethanolamine, ethanolamine, ethyldiamine, meglumine, tromethamine or procaine, or an acid addition salt such as a hydrochloride, hydrobromide, phosphate, acetate, fumarate, maleate, tartrate, citrate, oxalate, methanesulphonate or p-toluenesulphonate. Preferred salts include sodium and ammonium salts.

The compounds of formula (I) above may be converted to a pharmaceutically acceptable salt or solvate thereof. Preferred salts include sodium salts.

In a further aspect the invention provides a process for the preparation of a compound of formula (I) which comprises reaction of a compound of formula (II):

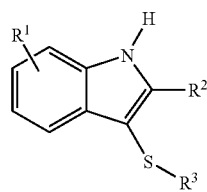

(II)

in which $R^1$, $R^2$ and $R^3$ are as defined in formula (I) or are protected derivatives thereof with a compound of formula (A):

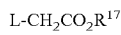 (A)

where $R^{17}$ is an ester forming group and L is a leaving group in the presence of a base, and optionally thereafter in any order
  removing any protecting group
  hydrolysing the ester group $R^{17}$ to the corresponding acid
  forming a pharmaceutically acceptable salt.

The reaction can be carried out in a suitable solvent such as THF using a base such as sodium hydride or the like. Suitable groups $R^{17}$ include $C_{1-6}$ alkyl groups such as methyl, ethyl or tertiary-butyl. Suitable L is a leaving group such as halo, in particular bromo Preferably the compound of formula (A) is ethyl, methyl or tertiary-butyl bromoacetate.

Hydrolysis of the ester group $R^{17}$ can be carried out using routine procedures, for example by stirring with aqueous sodium hydroxide or trifluoroacetic acid.

It will be appreciated that certain functional groups may need to be protected using standard protecting groups. The protection and deprotection of functional groups is for example, described in 'Protective Groups in Organic Chemistry', edited by J. W. F. McOmie, Plenum Press (1973), and 'Protective Groups in Organic Synthesis', 3rd edition, T. W. Greene & P. G. M. Wuts, Wiley-Interscience (1999).

Compounds of formula (II) can be prepared by reacting a compound of formula (III) with a compound of formula (IV):

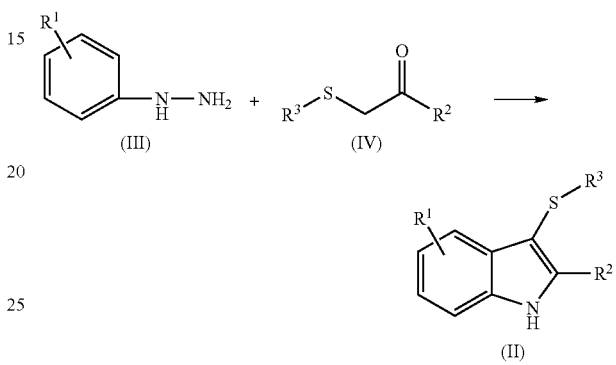

in which $R^1$, $R^2$ and $R^3$ are as defined in formula (I).

Preferably the reaction is carried out in acetic acid with heating.

Or, compounds of formula (II) can be prepared by reacting a compound of formula (V) with a compound of formula (IV).

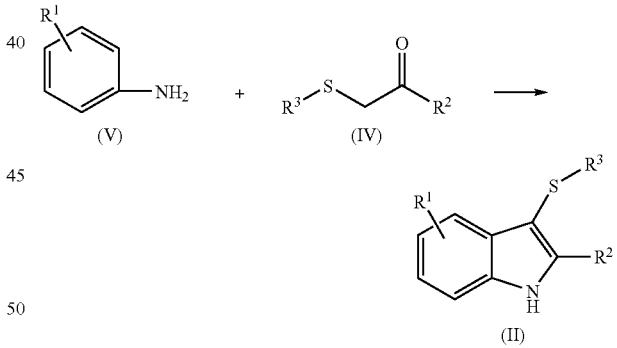

in which $R^1$, $R^2$ and $R^3$ are as defined in formula (I).

Preferably the reaction is carried out in a suitable solvent, such as dichloromethane or THF, using a chlorinating agent such as sulfonyl chloride or tert-butyl hypochlorite.[1]

Compounds of formulae (III), (IV) and (V) are commercially available or can be prepared using standard chemistry well known in the art.

Or, compounds of formula (I) can be prepared from compounds of formula (VI). The reaction is carried out with a compound of formula (B) in the presence of a halogenating agent, such as iodine, in a suitable organic solvent such as DMF.

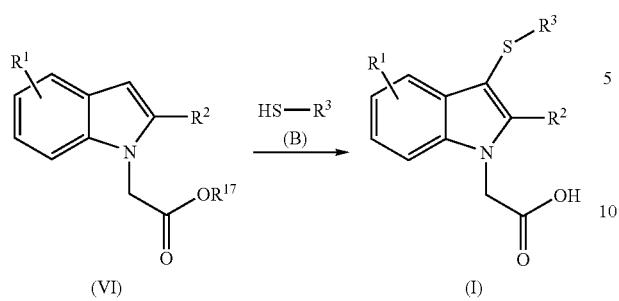

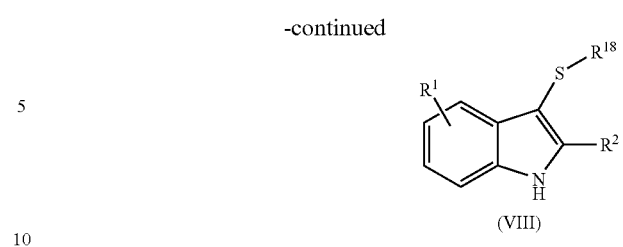

in which $R^1$, $R^2$, $R^3$ and $R^{17}$ are as defined in formulas (I) and (A) or protected derivatives thereof. The compound of formula (I) is obtained by hydrolysis using standard conditions as outlined previously.

Compounds of formula (VI) can be prepared from compounds of formula (VII) by reaction with a compound of formula (A) as outlined previously.

Or, compounds of formula (VII) can be converted to compounds of formula (I) by reaction with a compound of formula (B). The reaction is carried out in the presence of iodine, in a suitable organic solvent such as DMF. Sometimes the reaction is carried out in the presence of a base such as sodium hydride, after a period of stirring the reaction mixture is treated with a compound of formula (A) and subsequently hydrolysed. Alternatively an intermediate of formula (VIII) can be isolated and then reacted with a compound of formula (A) with subsequent hydrolysis.

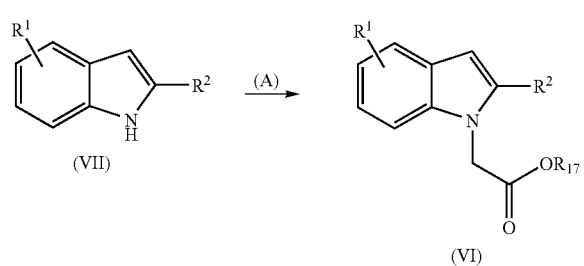

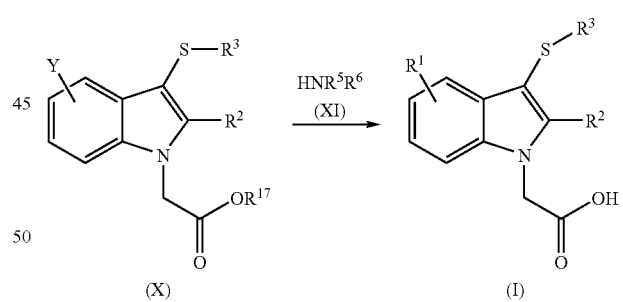

Some compounds of formula (VII) are commercially available or can be prepared from compounds of formula (VIII), by reaction with a compound of formula (B). The reaction is carried out in the presence of a thiol, preferably thiosalicylic acid in trifluoroacetic acid.

Or, compounds of formula (I) can be prepared from compounds of formula (X), by reaction with compounds of formula (XI).

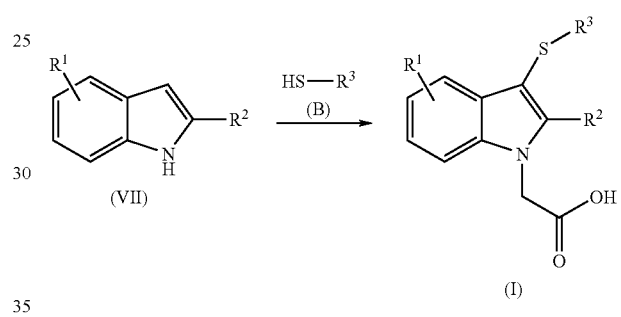

Compounds of formula (VIII) can be prepared by the reaction of a compound of formula (IV) with a compound of formula (IX), as described for the preparation of compounds of formula (II) previously, in which $R^1$, $R^2$ and $R^3$ are as defined in formula (II) or protected derivatives thereof. $R^{18}$ is $C_1$–$C_6$ alkyl (for example, methyl) or equivalent to $R^3$.

in which $R^1$, $R^2$, $R^3$, $R^5$, and $R^6$ are as defined in formula (I), and $R^{17}$ is as defined in formula (A) or protected derivatives thereof. Y is a halogen, preferably bromine or iodine. Preferably the reaction is carried out using Buchwald reaction conditions, using palladium catalysis. More preferably the catalyst used is $Pd_2(dba)_3$ with BINAP as a ligand. The reaction is carried out in toluene in the presence of a base, such as sodium tertiary butoxide at 110° C. The ester group $R^{17}$ is subsequently hydrolysed as previously outlined.

Or, compounds of formula (I) can be made from compounds of formula (X), by reaction with a compound of formula (XII).

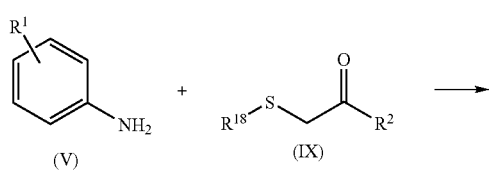

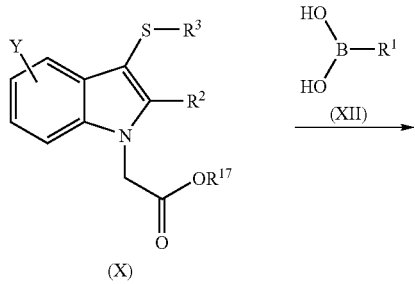

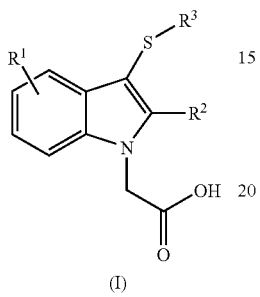

in which $R^1$, $R^2$, $R^3$, $R^5$, and $R^6$ are as defined in formula (I), and $R^{17}$ is as defined in formula (A) or protected derivatives thereof. Y is a halogen, preferably bromine or iodine. Preferably the reaction is carried out using Suzuki coupling reaction conditions, using palladium catalysis, the catalyst used is $Pd(PPh_3)_4$. The reaction is carried out in ethanol and toluene in the presence of a base, such as sodium hydrogen carbonate at reflux. The ester group $R^{17}$ is subsequently hydrolysed as previously outlined.

Compounds of formula (X) are prepared from compounds of formula (II) by reaction with a compound of formula (A) as outlined above.

Compounds of formula (XI) and (XII) are commercially available or can be prepared by is methods well known in the art.

Certain compounds of formula (II), (VI) (VIII) and (X) are believed to be novel and form a further aspect of the invention.

In a further aspect the invention provides a compound of formula (IA) which is a sub-class of formula (I):

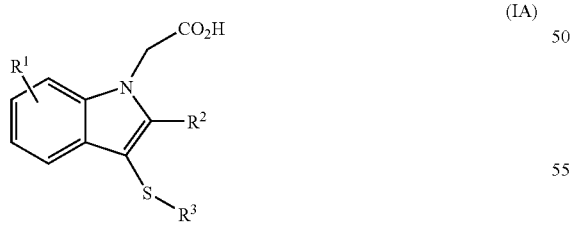

in which $R^1$ and $R^2$ are independently hydrogen, halogen, CN, amino, nitro, $C_{1-6}$alkyl, $C_{1-6}$alkoxy, $SO_2C_{1-6}$alkyl or $CONR^4R^5$ where $R^4$ and $R^5$ independently hydrogen or $C_{1-6}$alkyl; and $R^3$ is phenyl or heteroaryl, each of these groups being optionally substituted by one or more substituents selected from halogen, $C_{1-6}$alkyl, $C_{1-6}$alkoxy, $SO_2C_{1-6}$alkyl, CN, amino, or $CONR^4R^5$ where $R^4$ and $R^5$ independently hydrogen or $C_{1-6}$alkyl, and pharmaceutically acceptable salts thereof.

In a further aspect, the present invention provides the use of a compound of formula (I), a prodrug, pharmaceutically acceptable salt or solvate thereof for use in therapy.

The compounds of formula (I have activity as pharmaceuticals, in particular as modulators of CRTh2 receptor activity, and may be used in the treatment (therapeutic or prophylactic) of conditions/diseases in human and non-human animals which are exacerbated or caused by excessive or unregulated production of $PGD_2$ and its metabolites. Examples of such conditions/diseases include:

(1) (the respiratory tract) obstructive airways diseases including: asthma (such as bronchial, allergic, intrinsic, extrinsic and dust asthma particularly chronic or inveterate asthma (e.g. late asthma and airways hyper-responsiveness)); chronic obstructive pulmonary disease (COPD)(such as irreversible COPD); bronchitis (including eosinophilic bronchitis); acute, allergic, atrophic rhinitis or chronic rhinitis (such as rhinitis caseosa, hypertrophic rhinitis, rhinitis purulenta, rhinitis sicca), rhinitis medicamentosa, membranous rhinitis (including croupous, fibrinous and pseudomembranous rhinitis), scrofoulous rhinitis, perennial allergic rhinitis, easonal rhinitis (including rhinitis nervosa (hay fever) and vasomotor rhinitis); nasal polyposis; sarcoidosis; farmer's lung and related diseases; fibroid lung; idiopathic interstitial pneumonia; cystic fibrosis; antitussive activity, treatment of chronic cough associated with inflammation or iatrogenic induced;

(2) (bone and joints) arthrides including rheumatic, infectious, autoimmune, seronegative, spondyloarthropathies (such as ankylosing spondylitis, psoriatic arthritis and Reiter's disease), Behcet's disease, Sjogren's syndrome and systemic sclerosis;

(3) (skin and eyes) psoriasis, atopical dermatitis, contact dermatitis, other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, chronic skin ulcers, uveitis, Alopecia greatacorneal ulcer and vernal conjunctivitis;

(4) (gastrointestinal tract) Coeliac disease, proctitis, eosinopilic gastro-enteritis, mastocytosis, Crohn's disease, ulcerative colitis, irritable bowel disease; food-related allergies which have effects remote from the gut, (such as migraine, rhinitis and eczema);

(5) (central and peripheral nervous system) Neurodegenerative diseases and dementia disorders (such as Alzheimer's disease, amyotrophic lateral sclerosis and other motor neuron diseases, Creutzfeldt-Jacob's disease and other prion diseases, HIV encephalopathy (AIDS dementia complex), Huntington's disease, frontotemporal dementia, Lewy body dementia and vascular dementia), polyneuropathies (such as Guillain-Barré syndrome, chronic inflammatory demyelinating polyradiculoneuropathy, multifocal motor neuropathy), plexopathies, CNS demyelination (such as multiple sclerosis, acute disseminated/haemorrhagic encephalomyelitis, and subacute sclerosing panencephalitis), neuromuscular disorders (such as myasthenia gravis and Lambert-Eaton syndrome), spinal diorders (such as tropical spastic paraparesis, and stiff-man syndrome), paraneoplastic syndromes (such as cerebellar degeneration and encephalomyelitis), CNS trauma, migraine and stroke.

(6) (other tissues and systemic disease) atherosclerosis, acquired Immunodeficiency Syndrome (AIDS), lupus erythematosus; systemic lupus, erythematosus; Hashimoto's thyroiditis, type I diabetes, nephrotic syndrome, eosinophilia fascitis, hyper IgE syndrome, lepromatous leprosy, idiopathic thrombocytopenia pupura; post-operative adhesions, sepsis and ischemic/reperfusion injury in the heart, brain, peripheral limbs hepatitis (alcoholic, steatohepatitis and chronic viral), glomerulonephritis, renal impairment, chronic renal failure and other organs (7) (allograft rejection) acute and chronic following, for example, transplantation of kidney, heart, liver, lung, bone marrow, skin and cornea; and chronic graft versus host disease;

(8) Diseases associated with raised levels of $PGD_2$ or its metabolites.

Thus, the present invention provides a compound of formula (I), or a pharmaceutically-acceptable salt or solvate thereof, as hereinbefore defined for use in therapy.

Preferably the compounds of the invention are used to treat diseases in which the chemokine receptor belongs to the CRTh2 receptor subfamily.

Particular conditions which can be treated with the compounds of the invention are asthma, rhinitis and other diseases in which raised levels of $PGD_2$ or its metabolites. It is preferred that the compounds of the invention are used to treat asthma.

In a further aspect, the present invention provides the use of a compound of formula (I), or a pharmaceutically acceptable salt or solvate thereof, as hereinbefore defined in the manufacture of a medicament for use in therapy.

In a further aspect, the present invention provides the use of a compound or formula (I), or a pharmaceutically acceptable salt or solvate thereof; as hereinbefore defined in the manufacture of a medicament for use in therapy in combination with drugs used to treat asthma and rhinitis (such as inhaled and oral steroids, inhaled β2-receptor agonists and oral leukotriene receptor antagonists).

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of CRTh2 receptor activity is beneficial.

In the context of the present specification, the term "therapy" also includes "prophylaxis" unless there are specific indications to the contrary. The terms "therapeutic" and "therapeutically" should be construed accordingly.

The invention still further provides a method of treating diseases mediated by PGD2 or its metabolites wherein the prostanoid binds to its receptor (especially CRTh2) receptor, which comprises administering to a patient a therapeutically effective amount of a compound of formula (I), or a pharmaceutically acceptable salt, solvate or prodrug thereof, as hereinbefore defined.

The invention also provides a method of treating an inflammatory disease, especially psoriasis, in a patient suffering from, or at risk of; said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated.

For the above-mentioned therapeutic uses the dosage administered will, of course, vary with the compound employed, the mode of administration, the treatment desired and the disorder indicated.

The compound of formula (I), prodrugs and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof as herein before defined, in association with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Preferably the compound of the invention is administered orally.

The present invention also provides a pharmaceutical composition comprising a compound of formula (I), or a pharmaceutically acceptable salt or solvate thereof, as herein before defined, in association with a pharmaceutically acceptable adjuvant, diluent or carrier.

The invention will now be illustrated by the following non-limiting examples in which, unless stated otherwise:

(i) the title and sub-titled compounds of the examples and methods were named using the ACD labs/name program (version 6.0) from Advanced Chemical Development Inc, Canada;

(ii) unless stated otherwise, reverse phase preparative HPLC was conducted using a Symmetry, NovaPak or Ex-Terra reverse phase silica column;

(iii) Flash column chromatography refers to normal phase silica chromatography (iv) solvents were dried with $MgSO_4$ or $Na_2SO_4$ (v) Evaporations were carried out by rotary evaporation in vacuo and work-up procedures were carried out after removal of residual solids such as drying agents by filtration;

(vi) Unless otherwise stated, operations were carried out at ambient temperature, that is in the range 18–25° C. and under an atmosphere of an inert gas such as argon or nitrogen;

(vii) yields are given for illustration only and are not necessarily the maximum attainable;

(viii) the structures of the end-products of the formula (1) were confirmed by nuclear (generally proton) magnetic resonance AMR) and mass spectral techniques; proton magnetic resonance chemical shift values were measured on the delta scale and peak multiplicities are shown as follows: s, singlet; d, doublet; t, triplet; m, multiplet; br, broad; q, quartet, quin, quintet;

(ix) intermediates were not generally fully characterised and purity was assessed by thin layer chromatography (ILC), high-performance liquid chromatography (BPLC), mass spectrometry (MS), infra-red (IR) or NMR analysis;

(x) mass spectra (MS): generally only ions which indicate the parent mass are reported when given, $^1$H NMR data is quoted in the form of delta values for major diagnostic protons, given in parts per million (ppm) relative to tetramethylsilane (TMS) as an internal standard;

(xi) the following abbreviations are used.

| | |
|---|---|
| EtOAc | Ethylacetate |
| DMF | N,N-Dimethyl formamide |
| NMP | N-methylpyrrolidine |
| THF | tetrahydrofuran |
| RT | room temperature |
| TFA | trifluoroacetic acid |

EXAMPLE 1

3-[(4-chlorophenyl)thio]-2,5-dimethyl-1H-indol-1-acetic acid i) 3-[(4-chlorophenyl)thio]-2,5-dimethyl-1H-indole-1-acetic acid, ethyl ester A stirred solution of 3-[(4-chlorophenyl)thio]-2,5-dimethyl-1H-indole (300 mg) in dry N,N-dimethylformamide (15 ml) was treated with sodium hydride (42 mg of a 60% dispersion in mineral oil). After 10 minutes the reaction was treated with ethyl bromoacetate (116 μl) and stirring continued for 24 hours. The reaction was poured into distilled water (200 ml) and extracted with diethyl ether (3×100 ml). The extracts were dried (MgSO$_4$), evaporated in vacuo and the residue purified by flash column chromatography eluting with 10% ethyl acetate in iso-hexane. The subtitle compound was obtained as a yellow solid (yield 130 mg).

$^1$H NMR CDCl$_3$: δ(1H, m), 7.17–7.03(4H, m), 6.94(2H, m), 4.85(2H, s), 4.22(2H, q), 2.46(3H, s), 2.40(3H, s), 1.26(3H, t).

ii) 3-[(4-chlorophenyl)thio]-2,5-dimethyl-1H-indole-1-acetic acid

A solution of the compound from step (i) (120 mg) in ethanol (5 ml) was treated with water (5 ml) and 2.5N sodium hydroxide solution (1 ml). The resultant suspension was stirred at 70° C. for 1 hour and the ethanol removed in vacuo. The aqueous residue was acidified with 2N hydrochloric acid and the precipitate filtered off and concentrated in vacuo to give the title compound as an off-white solid (Yield 102 mg).

$^1$H NMR d$_6$-DMSO: δ13.12(1H, br s), 7.41(1H, d), 7.27 (1H, m), 7.24(1H, m), 7.15(1H, m), 7.01–6.94(3H, m), 5.08(2H, s), 2.39(3H, s), 2.34(3H, s). M.pt. 219–221° C.

The examples 2–10 are examples of compounds of formula (I) and were prepared by the following general method:

To a solution of the appropriate aryl thiol (1 g) in dichloromethane (15 ml) was added triethylamine (1 molar equivalent) followed by 1-chloroacetone (1 molar equivalent). The reaction was stirred for 2 hours. The reaction was washed with water, dried (MgSO$_4$), filtered, and evaporated. To this product was added 1-(4-methylphenyl)hydrazine hydrochloride (1 molar equivalent) and acetic acid (15 ml). The reaction was heated at 70° C. for 5 hours. Evaporation of solvent and purification by reverse phase HPLC (with a gradient eluent system (25% MeCN/NH$_{3(aq)}$ (0.1%) to 95% MeCN//NH$_{3(aq)}$ (0.1%)) gave the following intermediate compounds of Table 1.

TABLE 1

| Intermediate | Name | MS: ES(−ve) (M − H) |
|---|---|---|
| (i) | 3-[(2-chloro-4-fluorophenyl)thio]-2,5-dimethyl-1H-indole | 304 |
| (ii) | 3-[(3-chloro-4-fluorophenyl)thio]-2,5-dimethyl-1H-indole | 304 |
| (iii) | 3-[(2-methoxyphenyl)thio]-2,5-dimethyl-1H-indole | 282 |
| (iv) | 3-[(3-fluorophenyl)thio]-2,5-dimethyl-1H-indole | 270 |
| (v) | 3-[(4-ethylphenyl)thio]-2,5-dimethyl-1H-indole | 280 |
| (vi) | 3-[(2-chlorophenyl)thio]-2,5-dimethyl-1H-indole | 286 |
| (vii) | 3-[(2,5-dichlorophenyl)thio]-2,5-dimethyl-1H-indole | 320 |
| (viii) | 3-[(4-fluorophenyl)thio]-2,5-dimethyl-1H-indole | 270 |
| (ix) | 3-[(4-chloro-2-methylphenyl)thio]-2,5-dimethyl-1H-indole | 300 |

These intermediate compounds were then N-alkylated and the ester hydrolysed in a similar manner to that of example 1. This gave the examples 2–10 of Table 2.

TABLE 2

| Example | Name | MS: ES(−ve) (M − H) |
|---|---|---|
| 2 | 3-[(2-chloro-4-fluorophenyl)thio]-2,5-dimethyl-1H-indol-1-acetic acid | 362 |
| 3 | 3-[(3-chloro-4-fluorophenyl)thio]-2,5-dimethyl-1H-indol-1-acetic acid | 362 |
| 4 | 3-[(2-methoxyphenyl)thio]-2,5-dimethyl-1H-indol-1-acetic acid | 340 |
| 5 | 3-[(3-fluorophenyl)thio]-2,5-dimethyl-1H-indol-1-acetic acid | 328 |
| 6 | 3-[(4-ethylphenyl)thio]-2,5-dimethyl-1H-indol-1-acetic acid | 338 |
| 7 | 3-[(2-chlorophenyl)thio]-2,5-dimethyl-1H-indol-1-acetic acid | 344 |
| 8 | 3-[(2,5-dichlorophenyl)thio]-2,5-dimethyl-1H-indol-1-acetic acid | 378 |
| 9 | 3-[(4-fluorophenyl)thio]-2,5-dimethyl-1H-indol-1-acetic acid | 328 |
| 10 | 3-[(4-chloro-2-methylphenyl)thio]-2,5-dimethyl-1H-indol-1-acetic acid | 358 |

EXAMPLE 11

3-[(4-chlorophenyl)thio]-4-cyano-2,5-dimethyl-1H-indole-1-acetic acid i) 3-[(4-chlorophenyl)thio]-2,5-dimethyl-1H-indole-4-carbonitrile A stirred solution of 1-[(4-chlorophenyl)thio]-acetone (6.14 g) in dry dichloromethane (150 ml) at −78° C. was treated with sulphuryl chloride (2.25 ml). After 30 min a prepared solution of N,N,N',N'-tetramethyl-1,8-naphthalenediamine (6.01 g) and 5-amino-2-chloro-benzonitrile (3.89 g) in dry dicholoromethane (80 ml) was added dropwise over 30 min. The mixture was stirred for a further 2 hours, after which triethylamine (4.26 ml) was added and the reaction allowed to reach room temperature. The reaction mixture was diluted with dichloromethane (200 ml), washed with water, 1N HCl and brine. The organic phase was dried (MgSO$_4$), evaporated in vacuo, and the residue purified by flash column chromatography eluting with iso-hexane and ethyl acetate (1:1) to give the sub-title compound (1 g).

$^1$H NMR CDCl$_3$: δ 12.52 (s,1H), 7.74 (d, 1H), 7.38 (dd, 1H), 7.29 (m, 2H), 6.97 (m, 2H), 3.29 (s, 3H).

The regioisomer, 5-chloro-3-[(4-chlorophenyl)thio]-2-methyl-1H-indole-6-carbonitrile (600 mg) was also obtained.

$^1$H NMR CDCl$_3$: δ 8.68 (1H, s), 7.69 (1H, s), 7.61 (1H, s), 7.15 (2H, dt), 6.91 (2H. dt), 2.57 (3H, s).

ii) 3-[(4-chlorophenyl)thio]-4-cyano-2,5-dimethyl-1H-indole-1-acetic acid, methyl ester To a stirred solution of sodium hydride (96.1 mg of 60% dispersion in mineral oil) in dry tetrahydrofuran (15 ml) was added 3-[(4-chlorophenyl)thio]-2,5-dimethyl-1H-indole-4-carbonitrile (400 mg) in dry tetrahydrofuran (5 ml). After 30 minutes the reaction was treated with methyl bromoacetate (177 μl) and stirring continued for 4 hours. The solvent was removed in vacuo, the residue redissolved in ethyl acetate, washed with water, brine, dried (MgSO$_4$), evaporated in vacuo and the residue purified by flash column chromatography eluting with 1:1 ethyl acetate and iso-hexane mixture. The sub-title compound was obtained as a yellow solid (360 mg).

$^1$H NMR CDCl$_3$: δ 7.37 (1H, d), 7.30 (1H, d), 7.18–7.13 (2H, m), 7.00–6.96 (2H, m), 4.92 (2H, s), 3.80 (3H, s), 2.55 (3H, s).

iii) 3-[(4-chlorophenyl)thio]-4-cyano-2,5-dimethyl-1H-indole-1-acetic acid

The product of step ii) 0.1 g, was dissolved in THF (5 ml) and NaOH (200 μl, 1.25M solution). After 3 hours flirter NaOH (200 μl, 1.25 M solution) was added and the reaction mixture was stirred overnight at room temperature. The reaction mixture was concentrated in vacuo and the residue dissolved in water. The solution was acidified with dilute HCl. The resulting precipitate was filtered to give the title compound as a white solid (86 mg).

$^1$H NMR DMSO: δ 7.99 (1H, d), 7.47 (1H, d), 7.38 (2H, dt), 7.3 (2H, dt), 6.98 (2H, dt), 5.25 (2H, s), 2.49 (3H, s). MS: APCI+[M+H] 390 M.pt. 237–238° C.

EXAMPLE 12

5-chloro-3-[(4-chlorophenyl)thio]-6-cyano-2-methyl-1H-indole-1-acetic acid i) 5-chloro-3-[(4-chlorophenyl)thio]-6-cyano-2-methyl-1H-indole-1-acetic acid, methyl ester The sub-title compound was prepared by the method of example 11 part ii) using the product of example 11 part i).

ii) 5-chloro-3-[(4-chlorophenyl)thio]-6-cyano-2-methyl-1H-indole-1-acetic acid The title compound was prepared by the method of example 11 part iii) using the product of part i).

$^1$H NMR DMSO: δ 8.42 (1H, s), 7.59 (1H, s), 7.3 (2H, dt), 6.99 (2H, dt), 5.24 (2H, s), 2.46 (3H, s).

EXAMPLE 13

3-[(4-chlorophenyl)thio]-4-(ethylsulfonyl)-7-methoxy-2-methyl-1H-indole-1-acetic acid i) 3-[(4-chlorophenyl)thio]-4-(ethylsulfonyl)-7-methoxy-2-methyl-1H-indole

The sub-title compound was prepared by the method of example 11 part i) from 3-amino-4-methoxyphenylethyl sulfone.

$^1$H NMR CDCl$_3$: δ 9.00 (1H, s), 7.91 (1H, d), 7.12 (2H, dd), 6.86 (2H, m), 6.73 (1H, d), 4.05 (3H, s), 4.05 (3H, s), 3.46 (2H, q), 2.46 (3H, s) and 1.16 (3H, t).

ii) 3-[(4-chlorophenyl)thio]-4-(ethylsulfonyl)-7-methoxy-2-methyl-1H-indole-1-acetic acid, methyl ester The sub-title compound was prepared by the method of example 11 part ii) from the product of step i).

$^1$H NMR CDCl$_3$: δ 7.92 (1H, d), 7.13 (2H. dt), 6.85 (2H, dt), 6.73 (1H, d), 5.27 (2H, s), 3.98 (3H, s), 3.79 (3H, s), 3.48 (2H, q), 2.38 (3H, s) and 1.18 (3H, t).

iii) 3-[(4-chlorophenyl)thio]-4-(ethylsulfonyl)-7-methoxy-2-methyl-1H-indole-1-acetic acid The sub-title compound was prepared by the method of example 11 part iii) from the product of step ii).

$^1$H NMR DMSO: δ 7.72 (1H, d), 7.24 (2H, m), 6.96 (1H, d), 6.86 (2H, dt), 5.29 (2H, s), 5.27 (2H, s), 3.97 (3H, s), 3.41 (2H, q), 2.34 (3H, s) and 1.01 (3H, t).

EXAMPLE 14

3-[(4-chlorophenyl)thio]-4-[(diethylamino)sulfonyl]-7-methoxy-2-methyl-1H-indole-1-acetic acid i) 3-[(4-chlorophenyl)thio]-N,N-diethyl-7-methoxy-2-methyl-1H-indole-4-sulfonamide The sub-title compound was prepared by the method of example 11 part i) from 3-amino-N,N-diethyl-4-methoxy-benzenesulfonamide.

$^1$H NMR CDCl$_3$: δ 7.80 (1H, d), 7.88 (1H, s), 7.08(2H, d), 6.85 (2H, d), 6.66 (1H, d), 4.04 (3H, s), 3.25 (4H, q), 3.79 (3H, s), 2.43 (3H, s) and 0.98 (6H, t).

ii) 3-[(4-chlorophenyl)thio]-4-[(diethylamino)sulfonyl]-7-methoxy-2-methyl-1H-indole-1-acetic acid, methyl ester The sub-title compound was prepared by the method of example 11 part ii) from the product of step i), used directly without any further purification.

iii) 3-[(4-chlorophenyl)thio]-4-[(diethylamino)sulfonyl]-7-methoxy-2-methyl-1H-indole-1-acetic acid The sub-title compound was prepared by the method of example 11 part iii) from the product of step ii).

m.pt. 247–249° C. $^1$H NMR DMSO: δ 7.56 (1H, d), 7.18 (2H, dt), 6.85–6.79 (3H, m), 5.13 (2H, s), 3.94 (3H, s), 3.14 (4H, q), 2.29 (3H, s) and 0.88 (6H, t).

EXAMPLE 15

4-chloro-3-[(4-chlorophenyl)thio]-2-methyl-1H-indole-1-acetic acid i) 4-chloro-3-[4(-chlorophenyl)thio]-2-methyl-1H-indole

To a suspension of (3-chlorophenyl)-hydrazine hydrochloride (2 g) in acetic acid (30 ml) was added 1-[(4-chlorophenyl)thio]-acetone (2.24 g), acetonitrile (20 ml) and water (10 ml). The mixture was stirrred at room temperature overnight. The reaction mixture was concentrated in vacuo and the residue suspended in EtOAc, washed with sodium hydrogen carbonate solution, brine, dried (MgSO$_4$) and concentrated in vacuo. The residue was dissolved in acetic acid (20 ml) and heated to 80° C. overnight. The reaction mixture was poured into water, basified using NaOH and the organics extracted into EtOAc. The EtOAc was washed with brine, dried (MgSO$_4$) and concentrated in vacuo. Purification by Flash column chromatography (10% EtOAc/hexane as eluent) gave the sub-title compound (0.816 g).

$^1$H NMR CDCl$_3$: δ 8.38 (s, 1H), 7.27–7.23 (m, 1H), 7.14–7.07 (m, 4H), 6.96 (dt, 2H), 2.52 (s, 3H)

ii) 4-chloro-3-[(4-chlorophenyl thio]-2-methyl-1H-indole-1-acetic acid, methyl ester To a solution of the product from part (i) (0.2 g) in THF (5 ml) was added 1.0M sodium bis(trimethylsilyl)amide solution in THF (0.65 ml). The mixture was stirred for 30 minutes before methyl bromoacetate (62 µl) was added, the reaction was stirred at room temperature overnight. A further 0.3 ml of 1.0M sodium bis(trimethylsilyl)amide solution in THF and 30 µl of methyl bromoacetate was added to the mixture and was stirred for a further 3 hours. The mixture was then purified by flash column chromatography (14% EtOAc/hexane as eluent) to give sub-title compound (0.21 g).

$^1$H NMR CDCl$_3$: δ 7.17–7.11 (m, 5H), 6.95 (dt, 2H), 4.89 (s, 2H), 3.78 (s, 3H), 2.49 (s, 3H)

iii) 4-chloro-3-[(4-chlorophenyl)thio]-2-methyl-1H-indole-1-acetic acid

To a solution of the product from part (ii) (0.11 g) in THF (5 ml) was added a 1.25M solution of NaOH (aq) (0.25 ml). The reaction was stirred overnight at room temperature. The reaction mixture was concentrated in vacuo and the residue dissolved/suspended in water. The pH was adjusted to 2 using dilute HCl (aq) and the organics extracted into EtOAc, washed with brine, dried over MgSO$_4$ and concentrated in vacuo. The residue was purified by solid phase extraction using NH$_2$ sorbent (2 g), eluting with acetonitrile followed by 10% trifluroroacetic acid/acetonitrile to give the title compound (0.06 g).

$^1$H NMR CDCl$_3$: δ 7.54 (dd, 1H), 7.27 (dt, 2H), 7.14 (d, 1H), 7.08 (dd, 1H), 6.95 (dt, 2H), 5.16 (s, 2H), 2.43 (s, 3H) MS: APCI–[M–H] 364 M.pt. 184–187° C.

EXAMPLE 16

5-chloro-3-[(4-chlorophenyl)thio]-2-methyl-1H-indole-1-acetic acid i) 5-chloro-3-[4(-chlorophenyl)thio]-2-methyl-1H-indole

The sub-title compound was prepared by the method of example 15 part (i) using (4-chlorophenyl)-hydrazine hydrochloride. Product purified using flash column chromatography (20% EtOAc/hexane as eluent).

$^1$H NMR CDCl$_3$: δ 8.31 (s, 1H), 7.48 (d, 1H), 7.26 (m, 2H), 7.13 (m, 3H), 6.93 (m, 2H), 2.51 (s, 3H).

ii) 5-chloro-3-[(4-chlorophenyl)thio]-2-methyl-1H-indole-1-acetic acid, methyl ester The sub-title compound was prepared by the method of example 15 part (ii) using the product from part (i).

$^1$HNMR CDCl$_3$: δ 7.52 (d,1H), 7.27 (d, 1H), 7.20–7.10 (m, 3H), 6.97–6.89 (m, 2H), 4.80 (d, 2H), 3.79 (d, 3H), 2.47(d, 3H).

iii) 5-chloro-3-[(4-chlorophenyl)thio]-2-methyl-1H-indole-1-acetic acid

To a solution of the product from part (ii) (0.11 g) in THF (5 ml) was added a 1.25 M solution of NaOH (aq) (0.25 ml). The reaction was stirred overnight at room temperature. The reaction mixture was concentrated in vacuo and the residue dissolved/suspended in water. The pH was adjusted to 2 using dilute HCl (aq) and the solid which precipitated was isolated by filtration and dried under vaccum at 40° C. to give the title compound.

$^1$H NMR CDCl$_3$: δ 7.60 (d, 1H), 7.32–7.26 (m, 3M), 7.19 (dd, 1H), 6.98 (dt, 2H), 5.15 (s, 2H), 2.42 (s, 3H). MS: APCI–[M–H] 364 M.pt. decomposed>211° C.

EXAMPLE 17

6-chloro-3-[(4-chlorophenyl)thio]-2-methyl-1H-indole-1-acetic acid i) 6-chloro-3-[4(-chlorophenyl)thio]-2-methyl-1H-indole

The sub-title compound was prepared by the method of example 15 part (i).

$^1$H NMR CDCl$_3$: δ 8.27 (s, 2H), 7.39 (d, 1H), 7.34 (d, 1H), 7.10 (m, 3H), 6.92 (m, 2H), 2.50 (s, 3H).

ii) 6-chloro-3-[(4-chlorophenyl)thio]-2-methyl-1H-indole-1-acetic acid, methyl ester The sub-title compound was prepared by the method of example 15 part (ii) using the product from part (i).

$^1$H N CDCl$_3$: δ 7.43 (d, 1H), 7.27–7.25 (m, 1H), 7.14–7.09 (m, 3H), 6.92 (dd, 2H), 4.85 (s, 2H), 3.80 (d, 3H), 2.46 (d, 3H).

iii) 6-chloro-3-[(4-chlorophenyl)thio]-2-methyl-1H-indole-1-acetic acid

The title compound was prepared by the method of example 16 part (iii) using the product from part (ii).

¹H NMR CDCl₃: δ 7.71 (d, 1H), 7.33 (d, 1H), 7.26 (dt. 2H), 7.09 (dd, 1H), 6.96 (dt, 2H), 5.08 (s, 2H), 2.40 (s, 3H). MS: APCI−[M−H] 364 M.pt. decomposed>189° C.

EXAMPLE 18

7-chloro-3-[(4-chlorophenyl)thio]-2-methyl-1H-indole-1-acetic acid i) 7-chloro-3-[4(-chlorophenyl)thio]-2-methyl-1H-indole The sub-title compound was prepared by the method of example 15 part (i) using (2-chlorophenyl)-hydrazine hydrochloride. The product purified using Flash column chromatography (14% EtOAc/hexane as eluent).
¹H NMR CDCl₃: δ 8.48 (s 1H) 7.40 (d, 1H), 7.19 (m, 1H) 7.13–7.11 (m, 2H), 7.06 (t, 1H), 6.96–6.92 (m, 2H), 2.55 (s, 3H).

ii) 7-chloro-3-[(4-chlorophenol)thio]-2-methyl-1H-indole-1-acetic acid, methyl ester The sub-title compound was prepared by the method of example 15 part (ii) using the product from part (i).
¹HNMR CDCl₃: δ 7.44 (d, 1H), 7.18–7.09 (m, 3H), 7.03 (td, 1H), 6.92 (dd, 2H), 5.37 (2H, d), 3.81 (3H, d), 2.46 (3H, d).

iii) 7-chloro-3-[(4-chlorophenyl)thio]-2-methyl-1H-indole-1-acetic acid

The title compound was prepared by the method of example 16 part (iii) using the product from part (ii).
¹H NMR DMSO δ 7.35 (dd, 1H), 7.28 (dt, 2H), 7.20 (dd, 1H), 7.07 (t, 1H). 6.98 (dt, 2H), 5.36 (s, 2H), 2.45 (s, 3H). MS: APCI−[M−H] 364 M.pt. decomposes>207° C.

EXAMPLE 19

3-[(4-chlorophenyl)thio]-2-methyl-5-(methylsulfonyl)-1H-indole-1-acetic acid i) 3-[(4-chlorophenyl)thio]-2-methyl-5-(methylsulfonyl)-1H-indole The sub-title compound was prepared by the method of example 11 step i) from 4-methylsulphonyl-aniline hydrochloride.
¹H NMR CDCl₃: δ 8.78 (1H, s), 8.16 (1H,d), 7.74 (1H, dd), 7.47 (1H, d), 7.13 (2H, dt), 6.92 (2H, dt), 3.06 (3H, s), 2.55 (3H, s).

ii) 3-[(4-chlorophenyl)thio]-2-methyl-5-(methylsulfonyl)-1H-indole-1-acetic acid, methyl ester The sub-title compound was prepared by the method of example 11 step ii) from the product of step i).
¹HNMR CDCl₃: δ 8.20 (1H, d), 7.79 (1H, dd), 7.38 (1H, d), 7.14 (1H, dd), 6.92 (2H, dd), 4.96 (2H,s), 3.79 (3H, d), 2.52 (3H, s).

iii) 3-[(4-chlorophenyl)thio]-2-methyl-5-(methylsulfonyl)-1H-indole-1-acetic acid The product of part ii) (190 mg) was treated with methanol (10 ml), LiOH (18.9 mg) and water (2 ml). The reaction mixture was stirred for 4 hours. The reaction mixture was concentrated in vacuo and the residue was dissolved in water, acidified HCl to give the title compound as a white solid, 44 mg.
¹H NMR CDCl₃: δ 8.19 (1H, d), 7.79 (1H, dd), 7.39 (1H, d), 7.13 (1H, dd), 6.91 (2H, dd), 4.98 (2H,s), 3.04 (3H, s), 2.53 (3H, s). M.pt. 185–187° C.

EXAMPLE 20

2-dimethyl-3-[[4-(methylsulfonyl)phenyl]thio]-1H-indole-1-acetic acid i) 3-[(4-chlorophenyl)thio]-2-methyl-4-(methylsulfonyl)-1H-indole and 3-[(4-chlorophenyl)thio]-2-methyl-6-(methylsulfonyl)-1H-indole The sub-title compound was prepared by the method of example 19 part i) from 3-(methylsulfonyl)aniline hydrochloride to give a mixture of 3-[(4-chlorophenyl)thio]-2-methyl-6-(methylsulfonyl)-1H-indole and 3-[(4-chlorophenyl)thio]-2-methyl-4-(methylsulfonyl)-1H-indole. These were purified by Flash silica chromotography with 50% EtOAc/Hexane as eluent. This have the title product:
¹H NMR DMSO: δ 7.77 (2H, ddd), 7.33 (2H, t), 7.24 (2H, dt), 6.87 (2H, dt), 3.32 (3H, s), 2.40 (3H, s).
In addition 3-[(4-chlorophenyl)thio]-2-methyl-6-(methylsulfonyl)-1H-indole was also isolated. This isomer was used in example 2 step i.
¹H NMR DMSO: δ 12.30(1H, s), 7.93(1H, d), 7.50–7.59 (2H, m), 7.27(2H, dd), 6.95–7. (2H,m), 3.19(3H, s), 2.52 (3H, s).

ii) 2,5-dimethyl-3-[[4-(methylsulfonyl)phenyl]thio]-1H-indole-1-acetic acid

To the product of Example 21 step i (0.28 g) dissolved in THF (5 ml) was added NaH (63 mg, 60% dispersion in oil) and the reaction left to stir for 10 minutes. Ethyl bromoacetate (0.13 ml) was added and the reaction left to stir for 3 hours. EtOH (2 ml) and NaOH (2 ml, 10% aqueous) was added and the reaction left to stir for 30 mins. Evaporation of EtOH followed by addition of HCl (1M) gave a white precipitate. This was filtered and washed with diethyl ether to gave the title product as a solid (0.351 g).
¹H NMR DMSO: δ 13.33 (1H, s), 8.02 (1H, dd), 7.81 (1H, dd), 7.40 (1H, t), 7.24 (2H, dt), 6.89 (2H, dt), 5.29 (2H, s), 3.32 (3H, s), 2.39 (3H, s) MS: APCI+[M+DMSO] 488

EXAMPLE 21

2-methyl-3-[(4-methylphenyl)thio]-6-(methylsulfonyl)-1H-indole-1-acetic acid i) 2-methyl-3-[(4-methylphenyl)thio]-6-(methylsulfonyl)-1H-indole-1-acetic acid, ethyl ester To a stirred solution of sodium hydride (45 mg of 60% dispersion in mineral oil) in dry tetrahydrofuran (10 ml) was added 3-[(4-chlorophenyl)thio]-2-methyl-6-(methylsulfonyl)-1H-indole (160 mg) (the product of Example 20 step i). After 30 minutes the reaction was treated with ethyl bromoacetate (78 μl) and stirring continued for 1 hour. Reaction was quenched with ethanol, the solvent was removed in vacuo, the residue redissolved in ethyl acetate, washed with water, dried (MgSO₄), and evaporated in vacuo and the residue purified by flash column chromatography eluting with 30% ethyl acetate and iso-hexane mixture. The sub-title compound was obtained as a white solid (180 mg).
MS: ES+[M+H] 438.

ii) 2-methyl-3-[(4-methylphenyl thio]-6-(methylsulfonyl)-1H-indole-1-acetic acid The product of step ii) (180 mg), was dissolved in ethanol (5 ml) and NaOH (1 ml of a 10% solution) was added After 1 hour the reaction mixture was concentrated in vacuo and the residue dissolved in water. The solution was acidified with aqueuses HCl (1M) and exctracted with ethylaceate, washed with water, dried (MgSO$_4$), and evaporated in vacuo. The product was purified using NH$_2$ resin (0.5 g), loaded in MeCN and freed with 5% acetic acid/MeCN, to give 30 mg of product as a white solid.
$^1$H NMR DMSO: δ 8.11 (1H, s), 7.50–7.62 (2H, m), 7.24–7.29 (2H, m), 6.98 (2H, dd), 4.96 (2H, s), 3.21 (3H, s), 2.48 (3H, s) MS: APCI+[M+DMSO] 488.

EXAMPLE 22

4-bromo-3-[(4-chlorophenyl)thio]-2-methyl-1H-indole-1-acetic acid i) 4-bromo-3-[4(-chlorophenyl)thio]-2-methyl-1H-indole

The sub-title compound was prepared by the method of example 15 part (i) using (3-bromophenyl)-hydrazine hydrochloride. The product purified using flash column chromatography (10% EtOAc/hexane as eluent).
$^1$H NMR CDCl$_3$ δ 7.31 (1H, s), 7.30 (2H, d), 7.13 (2H, dt), 7.02 (1H, t), 6.94 (2H, dt), 2.52 (3H, s).

ii) 4-bromo-3-[(4-chlorophenyl)thio]-2-methyl-1H-indole-1-acetic acid, 1,1-dimethylethyl ester The sub-title compound was prepared by the method of example 11 part (ii) using the product of part (i) and t-butylbromoacetate. The product was purified using flash column chromatography (10% EtOAc/hexane as eluent).
$^1$H NMR CDCl$_3$: δ 7.31 (dd, 1H), 7.21 (dd, 1H), 7.14–7.10 (m, 2H), 7.05 (t, 1H), 6.94–6.91 (m, 2H), 4.77 (s, 2H), 2.49 (s, 3H), 1.43 (s, 9H).

iii) 4-bromo-3-[(4-chlorophenyl)thio]-2-methyl-1H-indole-1-acetic acid

To a solution of the product from part (ii) (0.09 g) in dichloromethane (2 ml) was added trifluroacetic acid (0.1 ml). The reaction was strirred overnight at room temperature. The solid which had precipitated was isolated by filtration, washed with hexane and dried overnight under vaccum at 40° C. to give the title compound (0.025 g).
$^1$H NMR (DMSO) δ 7.59 (dd, 1H), 7.29–7.25 (m, 3H), 7.08 (t, 1H), 6.94 (dt, 2H), 5.16 (s, 2H), 2.43 (s, 3H). MS: APCI+[M+H] 411 M.pt. decomposes>213° C.

EXAMPLE 23

3-[(4-chlorophenyl)thio]-4-[4-[(1,1-dimethylethoxy)carbonyl]-1-piperazinyl]-2-methyl-1H-indole-1-acetic acid To a dry flask was charged the product from example 22 part (ii) (1 g), N-tert-Butoxycarbonylpiperazine (0.48 g), Pd$_2$(dba)$_3$ (3 mg), 2,2'-bis(diphenylphosphino)-1,1'-binapthyl Binap (10 mg) and toluene (5 ml). The reaction was heated to 110° C. for 1 hour then allowed to cool. The mixture was diluted with EtOAc, washed with water, dried over MgSO$_4$ and concentrated in vacuo. The residue was purified using Flash column chromatography (eluent 25% EtOAc/Hexane then 50% EtOAc/Hexane/1% Acetic acid). Further purification using reverse phase preparative HPLC (eluent MeCN/NH$_3$ (aq)) gave titled compound (0.021 g).
$^1$H NMR (DMSO) δ 7.22 (dt, 2H), 7.12 (d, 1H), 7.02 (t, 1H), 6.93 (dt, 2H), 6.66 (d, 1H), 4.57 (s, 2H), 3.33 (s, 4H), 2.79 (s, 4H), 2.36 (s, 3H), 1.39 (s, 9H). MS: APCI+[M+H] 516 M.pt. 173° C.

EXAMPLE 24

3-[(4-chlorophenyl)thio]-2-methyl(1-piperazinyl)-1H-indole-1-acetic acid i) 3-[(4-chlorophenyl)thio]-4-[4-[(1,1-dimethylethoxy)carbonyl]-1-piperazinyl]-2-methyl-1H-indole-1-acetic acid, 1,1-dimethylethyl ester The sub-title compound was prepared by the method of example 23. The product was purified by flash column chromatography (eluent 25% EtOAc/hexane).
$^1$H NMR (DMSO) 90° C. δ 7.21–7.15 (m, 3H), 7.08 (t, 1H), 6.92 (d, 2H), 6.72 (d, 1H), 4.99 (s, 2H), 3.26 (s, 4H), 2.81 (t, 4H), 2.40 (s, 3H), 1.40 (s, 18H).

ii) 3-[(4-chlorophenyl)thio]-2-methyl-4-(1-piperazinyl)-1H-indole-1-acetic acid To a solution of the product from part (i) (0.34 g) in dichloromethane (5 ml) was added 4M HCl in dioxan (1.3 ml), the mixture was stirred at room temperature overnight. The solid which precipitated was isolated by filtration, suspended in dichloromethane (20 ml) and trifluoroacetic acid was added (6 ml) and the reaction stirred for a further 18 hours. The mixture was concentrated in vacuo and the residue triturated with ether to give a solid. The solid was dried overnight at 40° C. under vacuum to giveb the title compound (0.2 g).
$^1$H NMR (DMSO) 90° C. δ 7.28–7.20 (m, 3H), 7.12 (t, 1H), 6.95 (d, 2H), 6.77 (d, 1H), 5.02 (s, 2H), 3.08 (d, 4H), 3.00 (d, 4H), 2.42 (s, 3H). MS: APCI−[M−H] 414 M.pt. decomposes>249° C.

EXAMPLE 25

5-bromo-[(4-chlorophenyl)thio]-2-methyl-1H-indole-1-acetic acid i) 5-bromo-3-[4(-chlorophenyl)thio]-2-methyl-1H-indole

The sub-title compound was prepared by the method of example 15 part (i) using (4-bromophenyl)-hydrazine hydrochloride. Product purified by flash column chromatography (eluent 10% EtOAc/hexane).
$^1$H NMR (CDCl$_3$) δ 8.31 (s, 1H), 7.64 (d, 1H), 7.28 (dd, 2H), 7.22 (d, 2H), 7.13 (m, 2H), 6.93 (dt, 2H), 2.51 (s, 3H). MS: APCI+[M+H] 352 ii) 5-bromo-3-[(4-chlorophenyl)thio]-2-methyl-1H-indole-1-acetic acid, 1,1-dimethylethyl ester The sub-title compound was prepared by the method of example 11 part (ii) using the product of part (i) and t-butylbromoacetate. Product was purified using flash column chromatography.

(10% EtOAc/hexane as eluent).

$^1$H NMR (DMSO) δ 7.54 (d,1H), 7.45 (d, 1H), 7.34–7.25 (m, 3H), 6.97 (m, 2H), 5.15 (s, 2H), 2.41 (s, 3H), 1.41 (s, 9H).

Addition of ethanol to the residue after evaporation resulted in by-product 5-bromo-3-[(4-chlorophenyl)thio]-2-methyl-1H-indole-1-acetic acid, ethyl ester also been obtained after chromatography.

$^1$H NMR (DMSO) δ 7.56 (d, 1H), 7.46 (d, 1H), 7.34–7.27 (m, 3H), 6.97 (dd, 2H), 5.27 (s, 2H), 4.17 (q, 2H), 2.41 (s, 3H), 1.21 (t, 3H).

iii) 5-bromo-3-[(4-chlorophenyl)thio]-2-methyl-1H-indole-1-acetic acid, sodium salt To a solution of the by-product from part (ii) (0.2 g) in ethanol (10 ml) was added a 1M solution of NaOH (aq) (0.5 ml). The reaction was stirred overnight at room temperature. The reaction mixture was concentrated in vacuo and the residue recrystallised from boiling water. The solid was isolated by filtration, dried overnight at 40° C. under vaccum to give the title compound (0.13 g).

$^1$H NMR (DMSO) δ 7.39 (d, 1H), 7.37 (d, 1H), 7.26 (d, 2H), 7.21 (dd, 1H), 6.97 (dt, 2H), 4.47 (s, 2H), 2.38 (s, 3H).

EXAMPLE 26

3-[(4-chlorophenyl)thio]-2-methyl-5-phenyl-1H-indole-1-acetic acid i) 3-[(4-chlorophenyl)thio]-2-methyl-5-phenyl-1H-indole-1-acetic acid, ethyl ester To a solution of the product of example 25 part (ii) (0.5 g) in ethanol (0.8 ml) and toluene (3 ml) was added 2M sodium carbonate solution in water (1.4 ml), phenylboronic acid (0.131 g) and tetrakis(triphenylphosphine)palladium(0) (1.2 g). The reaction was heated to reflux for 2 hours, cooled and concentrated in vacuo. The residue was purified by flash column chromatography to give the subtitle compound (0.4 g). This was used in step (ii) without further characterisation.

ii) 3-[(4-chlorophenyl)thio]-2-methyl-5-phenyl-1H-indole-1-acetic acid

The title compound was prepared by the method of example 26 part (iii). Purification by reverse phase preparative HPLC gave the title compound.

$^1$H NMR (DMSO) δ 7.61–7.53 (4H, m,), 7.46–0.38 (3H, m), 7.31–7.22 (3H, m), 7.01 (2H, dd), 4.91 (2H, s), 2.42 (3H, s). MS: APCI–[M–H] 406

EXAMPLE 27

3-[(4-chlorophenyl)thio]-5-cyano-2-methyl-1H-indole-1-acetic acid i) 3-[(4-chlorophenyl)thio]-5-cyano-2-methyl-1H-indole To a stirred solution of 4-aminobenzonitrile (5 g) in dichloromethane (150 ml) cooled to −70° C. was added t-butyl hypochlorite (4.6 g) dropwise over 5 minutes. The reaction was stirred for 10 minutes before 1-[4-chlorophenyl)thio]-2-propanone (8.49 g) was added as a solution in dichloromethane (20 ml). After 1 hour triethylamine (5.9 ml) was added and the reaction allowed to warm to room temperature. The reaction was diluted with dichloromethane, washed with HCl (aq), brine, dried over MgSO$_4$, and concentrated in vacuo to give a brown solid. Purification by recrystallisation from Methanol gave the sub-title compound (7.5 g).

$^1$H NMR (CDCl$_3$) δ 8.61 (s, 1H), 7.84 (s, 1H), 7.44 (dd, 1H), 7.41 (d, 1H), 7.19–7.08 (m, 2H), 6.93 (dd, 2H), 2.56 (s, 3H).

ii) 3-[(4-chlorophenyl)thio]-5-cyano-2-methyl-1H-indole-acetic acid, ethyl ester The sub-title compound was prepared by the method of example 11 part (ii) using the product from part (i). Used without further characterisation in part (iii).

iii) 3-[(4-chlorophenyl)thio]-5-cyano-2-methyl-1H-indole-1-acetic acid

The title compound was prepared using the method pf example 16 part (iii) using the product from part (ii).

$^1$H NMR (DMSO) δ 13.34 (s, 1H), 7.82–7.77 (m, 2H), 7.57 (dd, 1H), 7.29 (dt, 2H), 7.02–6.98 (m, 2H), 5.23 (s, 2H), 2.46 (s, 3H). MS: APCI–[M–H] 355

EXAMPLE 28

3-[(4-Cyanophenyl)thio]-2,5-dimethyl-1H-indol-1-yl-acetic acid, ammonium salt i) (2,5-dimethyl-1H-indol-1-yl}acetic acid 60% sodium hydride/oil (0.64 g) was added to a solution of 2,5-dimethyl-1H-indole (2.0 g) in DMF (15 ml). After 15 min ethyl bromoacetate (2.7 ml) was added quickly and the reaction stirred for 20 min. The reaction mixture was quenched with 1% aqueous acetic acid (100 ml), extracted with ethyl acetate (2×100 ml) and washed with water (2×50 ml) and brine (20 ml). The extracts were dried (MgSO$_4$), filtered and evaporated in vacuo to yield a brown solid. The solid was dissolved in EtOH (20 ml) and aqueous sodium hydroxide (1M,10 ml) added. After 1 hour the solution was adjusted to pH6 with aqueous hydrochloric acid (1M,~10 ml), and then evaporated in vacuo. The residue was purified by flash column chromatography (gradient 1–10% methanol in dichloromethane). The sub-title compound was obtained as a red/brown solid (1.3 g).

MS (APCI+) 204 [M+H]$^+$ $^1$H NMR DMSO-d6: δ 7.22–7.17 (2H, m), 6.85 (1H, d), 6.11 (1H, s), 4.87 (2H, s), 2.34 (3H, s), 2.30 (3H, s)

ii) {3-[(4-Cyanophenyl)thio]-2,5-dimethyl-1H-indol-1-yl}acetic acid, ammonium salt Iodine (0.51 g) was added to a solution of 4-cyanobenzenethiol (0.27 g) and the product from example 28 step i) (0.2 g) in DMF (5 ml). After 1 hour the solution was purified by reverse phase HPLC. The solvent was evaporated in vacuo and the oily residue treated with ether to give a solid. Filtered off and dried to yield the title compound as a white solid (0.25 g).

MS: APCI-[(M-NH$_4$)-H]$^-$ 334 $^1$H NMR DMSO-d6: δ 7.62 (2H, d), 7.35 (1H, d), 7.10 (1H, s), 7.08 (2H, d), 6.97 (1H, d), 4.80 (2H, s), 2.36 (3H, s), 2.32 (3H, s)

EXAMPLE 29

3-[(3-methoxyphenyl)thio]-2,5-dimethyl-1H-indole-1-acetic acid

Iodine (0.51 g) was added to a solution of 3-methoxylbenzenethiol (0.25 g) and the product from example 28 step i) (0.2 g) in DMF (5 ml). After 1 hour the solution was purified by reverse phase HPLC. The solvent was evaporated in vacuo and the oily residue treated with ether to give a solid. Filtered off and dried to yield the title compound as a white solid (0.22 g).

MS: APCI-[(M-H]$^-$ 340 $^1$H NMR DMSO-d6: δ 7.40 (1H, d), 7.16 (1H, s), 7.11 (1H, t), 6.98 (1H, d), 6.63 (1H, d), 6.55 (1H, d), 6.45 (1H, s), 5.08 (2H, s), 3.61 (3H, s), 2.39 (3H, s), 2.34 (3H, s)

EXAMPLE 30

3-[(4-methoxyphenyl)thio]-2,5-dimethyl-1H-indole-1-acetic acid, ammonium salt

Iodine (0.51 g) was added to a solution of 4-methoxylbenzenethiol (0.25 g) and the product from example 28 step i) (0.2 g) in DMF (5 ml). After 1 hour the solution was purified by reverse phase HPLC. The solvent was evaporated in vacuo and the oily residue treated with ether to give a solid. Filtered off and dried to yield the title compound as a white solid (0.27 g).

MS: APCI-[(M-H]$^-$ 340 $^1$H NMR DMSO-d6: δ 7.24 (1H, d), 7.15 (1H, s), 6.95 (2H, d), 6.90 (1H, d), 6.78 (2H, d), 4.60 (2H, s), 3.66 (3H, s), 2.38 (3H, s) and 2.33 (3H, s).

EXAMPLE 31

3-[(3-ethylphenyl)thio]-2,5-dimethyl-1H-indole-1-acetic acid ammonium salt

Iodine (0.44 g) was added to a solution of 2-ethylbenzenethiol (0.32 g) and the product from example 28 step i) (0.2 g) in DMF (5 ml). After 1 hour the solution was purified by reverse phase HPLC. The solvent was evaporated in vacuo and the oily residue treated with ether to give a solid. Filtered off and dried to yield the title compound as a white solid (0.18 g).

MS APCI) [(M-NH$_4$)-H]$^-$ 338 $^1$H NMR DMSO-d6: δ 7.26 (1H, d), 7.16 (1H, d), 7.08 (1H, s), 7.01–6.85 (3H, m), 6.48 (1H, d), 4.57 (2H, s), 2.83 (2H, q), 2.34 (3H, s), 2.31 (3H, s), 1.31 (3H, t)

EXAMPLE 32

2,5-dimethyl-3-[(2-methylphenyl)thio]-1H-indole-1-acetic acid

Iodine (0.29 g) was added to a solution of 2-methylbenzenethiol (0.16 g) and the product from example 28 step i) (0.2 g) in DMF (5 ml). After 1 hour the solution was purified by reverse phase HPLC. The solvent was evaporated in vacuo and the oily residue treated with ether to give a solid. Filtered off and dried to yield the title compound as a white solid (0.16 g).

MS: APCI-[(M-H]$^-$ 324 $^1$H NMR DMSO-d6: δ 7.24 (1H, d), 7.15 (1H, d), 7.07 (1H, s), 6.97–6.86 (3H, m), 6.47 (1H, d), 4.49 (2H, s), 2.42 (3H, s), 2.33 (3H, s), 2.31 (3H, s)

EXAMPLE 33

3-[(3-chlorophenyl)thio]-2,5-dimethyl-1H-indole-1-acetic acid, sodium salt

Iodine (0.29 g) was added to a solution of 3-chlorobenzenethiol (0.175 g) and the product from example 28 step i) (0.2 g) in EtOH (5 ml). After 1 hour the solution was purified by reverse phase HPLC. The solvent was evaporated in vacuo to yield the product as a colourless oil. The oil was then dissolved in methanol (10 ml) treated with aqueous sodium hydroxide (1M, 0.52 ml) and evaporated in vacuo to yield the sodium salt as a white solid (0.19 g).

MS APCI-[(M-Na)-H]$^-$ 344 $^1$H NMR DMSO-d6: δ 7.28–7.15 (2H, m), 7.13–7.06 (2H, m), 6.97–6.88 (3H, m), 4.42 (2H, s), 2.36 (3H, s), 2.33 (3H, s)

EXAMPLE 34

3-[(2-Fluorophenyl)thio]-2,5-dimethyl-1H-indole-1-acetic acid, sodium salt

Iodine (0.51 g) was added to a solution of 2-fluorobenzenethiol (0.26 g) and the product from example 28 step i) (0.2 g) in DMF (5 ml). After 1 hour the solution was purified by reverse phase HPLC. The solvent was evaporated in vacuo to yield the product as a colourless oil. The oil was then dissolved in MeOH (10 ml) treated with aqueous sodium hydroxide (1M, 0.52 ml) and evaporated in vacuo to yield the sodium salt as a white solid (0.08 g).

MS APCI-[(M-Na)-H]$^-$ 328 $^1$H NMR DMSO-d6: δ 7.24 (1H, d), 7.18 (1H, m), 7.10 (1H, s), 7.09 (1H, m), 6.91 (1H, d), 6.56 (1H, m), 6.56 (1H, m), 4.42 (2H, s), 2.35 (3H, s), 2.33 (3H, s)

EXAMPLE 35

3-[(2,6-Dichlorophenyl)thio]-2,5-dimethyl-1H-indole-1-acetic acid

Iodine (0.51 g) was added to a solution of 2,6-dichlorobenzenethiol (0.36 g) and the product from example 28 step i) (0.2 g) in DMF (5 ml). After 1 hour the solution was purified by reverse phase HPLC. The solvent was evaporated in vacuo and the oily residue treated with ether to give a solid. Filtered off and dried to yield the title compound as a white solid (0.22 g).

MS APCI-[M-H]$^-$ 378 $^1$H NMR DMSO-d6: δ 7.49 (2H, d), 7.29 (1H, m), 7.24 (1H, d), 7.13 (1H, s), 6.88 (1H, d), 4.81 (2H, s), 2.44 (3H, s), 2.29 (3H, s)

EXAMPLE 36

3-(1H-Imidazol-2-ylthio)-2,5-dimethyl-1H-indole-1-acetic acid, ammonium salt Iodine (0.51 g) was added to a solution of 1H-imidazole-2-thiol (0.20 g) and the product from example 28 step i) (0.2 g) in DMF (5 ml). After 1 hour the solution was purified by reverse phase BPLC. The solvent was evaporated in vacuo and the oily residue treated with ether to give a solid. Filtered off and dried to yield the title compound as a white solid (0.23 g).

MS APCI-[M-H]$^-$ 300 $^1$H NMR DMSO-d6: δ 8.15 (1H, s), 7.21 (1H, d), 7.21 (2H, s), 6.90 (1H, d), 4.51 (2H, s), 2.40 (3H, s), 2.35 (3H, s)

EXAMPLE 37

2,5-Dimethyl-3-(1H-1,2,4-triazol-3-ylthio)-1H-indole-1-acetic acid

Iodine (0.51 g) was added to a solution of 1H-1,2,4-triazole-3-thiol (0.20 g) and the product from example 28 step i) (0.2 g) in DMF (5 ml). After 1 hour the solution was purified by reverse phase HPLC. The solvent was evaporated in vacuo and the oily residue treated with ether to give a solid. Filtered off and dried to yield the title compound as a white solid (0.24 g).

MS APCI-[M-H]$^-$ 301 $^1$H NMR DMSO-d6: δ 8.15 (1H, s), 7.21 (1H, d), 7.20 (1H, s), 6.90 (1H, d), 4.49 (2H, s), 2.40 (3H, s), 2.35 (3H, s)

EXAMPLE 38

2,5-Dimethyl-3-[(4-methyl-4H-1,2,4-triazol-3-yl)thio]-1H-indole-1-acetic acid Iodine (0.51 g) was added to a solution of 4-methyl-4H-1,2,4-triazole-3-thiol (0.20 g) and the product from example 28 step i) (0.2 g) in DMF (5 ml). After 1 hour the solution was purified by reverse phase HPLC. The solvent was evaporated in vacuo and the oily residue treated with ether to give a solid. Filtered off and dried to yield the title compound as a white solid (0.21 g).

MS APCI-[M-H]$^-$ 315 $^1$H NMR DMSO-d6: δ 8.44 (1H, s), 7.29 (1H, s), 7.19 (1H, d), 6.90 (1H, d), 4.46 (2H, s), 3.52 (3H, s), 2.46 (3H, s), 2.35 (3H, s)

EXAMPLE 39

2,5-Dimethyl-3-[(4-methyl-2-oxazolyl)thio]-1H-indole-1-acetic acid

Iodine (0.51 g) was added to a solution of 4-methyl-2-oxazolethiol (0.23 g) and the product from example 28 step i) (0.2 g) in DMF (5 ml). After 1 hour the solution was purified by reverse phase HPLC. The solvent was evaporated in vacuo and the oily residue treated with ether to give a solid. Filtered off and dried to yield the title compound as a white-solid (0.23 g).

MS APCI-[M-H]$^-$ 315 $^1$H NMR DMSO-d6: δ 7.69 (1H, s), 7.29 (1H, d), 7.22 (1H, s), 6.95 (1H, d), 4.78 (2H, s), 2.42 (3H, s), 2.36 (3H, s), 1.99 (3H, s)

EXAMPLE 40

2,5-dimethyl-3-[(1-methyl-1H-imidazol-2-yl)thio]-1H-indole-1-acetic acid

Iodine (0.51 g) was added to a solution of 1-methyl-1H-imidazole-2-thiol (0.23 g) and the product from example 28 step i) (0.2 g) in DMF (5 ml). After 1 hour the solution was purified by reverse phase HPLC. The solvent was evaporated in vacuo and the oily residue treated with ether to give a solid. Filtered off and dried to yield the title compound as a white solid (0.21 g).

MS APCI-[M-H]$^-$ 314 $^1$H NMR DMSO-d6: δ 7.37 (1H, s), 7.29 (1H, d), 7.15 (1H, s), 6.93 (1H, d), 6.84 (1H, s), 4.97 (2H, s), 3.60 (3H, s), 2.49 (3H, s), 2.36 (3H, s)

EXAMPLE 41

2,5-Dimethyl-3-[[4-(methylsulfonyl)phenyl]thio]-1H-indole-1-acetic acid, ammonium salt i) 4-(Methylsulfonyl)-benzenethiol

1-Fluoro-4-(methylsulfonyl)-benzene (1.74 g) and sodium hydrosulphide hydrate (0.67 g) were dissolved in DMF (10 ml) and stirred at room temperature for 24 hours. The reaction was quenched with water, acidified with 2M hydrochloric acid (20 ml) and extracted with ethyl acetate (2×50 ml). The combined extracts were then washed with water (2×25 ml) and brine (20 ml). The organic solution was dried (MgSO$_4$), filtered and evaporated in vacuo to yield the sub-title compound as a white solid (1.8 g).

MS: ESI+: [M+H] 188 $^1$H NMR CDCl$_3$: δ 7.99 (2H, d), 7.27 (2H, d), 3.05 (3H, s)

ii) 2,5-Dimethyl-3-[[4-(methylsulfonyl)phenyl]thio]-1H-indole-1-acetic acid, ammonium salt Iodine (0.51 g) was added to a solution of the product from example 41 step i) (0.565 g) and the product from example 28 step i) (0.2 g) in DMF (5 ml). After 1 hour the solution was purified by reverse phase HPLC. The solvent was evaporated in vacuo and the oily residue treated with ether to give a solid, which was filtered and dried to yield the title compound as a white solid (0.25 g).

MS: APCI-[M-H] 388 $^1$H NMR DMSO-d6: δ 7.69 (2H, d), 7.31 (1H, d), 7.15 (2H, d), 7.11 (1H, s), 6.95 (1H, d), 4.62 (2H, s), 3.13 (3H, s), 2.36 (3H, s), 2.33 (3H, s)

EXAMPLE 42

2,5-Dimethyl-3-(8-quinolinylthio)-1H-indole-1-acetic acid, hemi-ammonium salt Iodine (0.25 g) was added to a solution of 8-quinolinethiol (0.16 g) and the product from example 28 step i) (0.1 g) in DMF (5 ml). After 1 hour the solution was purified by reverse phase HPLC. The solvent was evaporated in vacuo and the oily residue treated with ether to give a solid, which was filtered and dried to yield the title compound as a white solid (0.08 g).

MS: APCI-[M-H] 361 $^1$H NMR DMSO-d6: δ 8.97 (1H, s), 8.37 (1H, d), 7.62 (2H, m), 7.32 (1H, d), 7.27 (1H, t), 7.08 (1H, s), 6.94 (1H, d), 6.71 (1H, d), 4.69 (2H, s), 2.36 (3H, s), 2.30 (3H, s)

EXAMPLE 43

3-[(4-Chlorophenyl)thio]-5-fluoro-2,4-dimethyl-1H-indole-1-acetic acid i) 7-Chloro-5-fluoro-2,4-dimethyl-3-methylthio-1H-indole

A stirred solution of 2-chlorofluoro-5-methylaniline (1.65 g) in methylene chloride (100 ml) under nitrogen was treated at −65° C. with a solution of $^t$butyl hypochlorite (1.13 g) in methylene chloride (5 ml), stirred at −65° C. for 10 min, treated at −65° C. with a solution of methylthioacetone (1.080 g) in methylene chloride (5 ml) stirred at −65° C. for 1 hour, treated at −65° C. with triethylamine (1.05 g) and allowed to reach ambient temperature. The solution was washed, dried ($MgSO_4$) and evaporated. The residue was purified by silica chromatography using 25% acetone in isohexane as eluent to give the title compound (1.7 g).

MS: APCI−[M−H] 242 $^1$H NMR DMSO-d6: δ 11.67 (1H, s), 7.07 (1H, d), 2.71 (3H, d), 2.48 (3H, s), 2.19 (3H, s).

ii) 7-Chloro-5-fluoro-2,4-dimethyl-1H-indole

A solution of the product from part i) (1.13 g) and thiosalicylic acid (1.43 g) in trifluoroacetic acid (50 ml) was stirred at 60° C. for 2 hours and evaporated. The residue was taken up in methylene chloride, washed with 1N aqueous sodium hydroxide solution followed by water, dried ($MgSO_4$) and evaporated. The residue was purified by silica chromatography using 10% ethyl acetate in isohexane as eluent to give the title compound (0.82 g).

MS: ESI 197 [M+H] $^1$H NMR DMSO-d6: δ 11.25 (1H, s), 6.97 (1H, d), 6.28 (1H, q), 2.40 (3H, d), 2.30 (3H, d)

iii) 5-Fluoro-2,4-dimethyl-1H-indole

A stirred suspension of 10% palladium on carbon (200 mg) in ethanol (50 ml) was treated with a solution of ammonium formate (2.3 g) in water (2 ml), stirred for 1 min, treated with a solution the the product from part ii) (721 mg) in ethanol (10 ml), stirred for 2 days, treated with more 10% palladium on carbon (500 mg), stirred at 40° C. for 2 hours and filtered. The solids were washed with ethanol and the combined filtrates were evaporated. The residue was taken in ether, washed, dried ($MgSO_4$) and evaporated to give the title compound.

MS: ESI+[M+H] 163 $^1$H NMR $CDCl_3$: δ 7.82 (1H, s), 7.04–7.01 (1H, m), 6.82 (1H, dd), 6.21—6.21 (1H, m), 2.45 (3H, s), 2.40—2.40 (3H, m).

iv) Methyl 5-Fluoro-2,4-dimethyl-1H-indol-1-yl]acetate

A stirred suspension of the product from step iii) (2 g) and cesium carbonate (4.8 g) in acetone (100 ml) was treated with methyl bromoacetate (4.22 g), heated under reflux overnight, treated with more cesium carbonate (2.4 g) and methyl bromoacetate (1.3 ml), heated under reflux for 2 hours and evaporated. The residue was taken up in ethyl acetate, washed with brine (3×), dried dried ($MgSO_4$) and evaporated. The residue was purified by silica chromatography using 20% acetone in isohexane as eluent to give the title compound as a white solid (2.57 g).

MS: APCI−[M−H] 253 BP 176° C. $^1$H NMR DMSO-d6: δ 6.92–6.83 (2H, m), 6.30 (1H, s), 4.76 (2H, s), 3.74 (3H, s), 2.40–2.39 (6H, m).

v) 5-Fluoro-2,4-dimethyl-1H-indol-1-yl]acetic acid

A stirred solution of the product from step iv) (2.51 g) in THF (50 ml) was treated with a solution of lithium hydroxide (894 mg) in water (10 ml), stirred overnight and concentrated to remove most of the THF. The residue was acidified with 1N hydrochloric acid and extracted with methylene chloride. The washed and dried ($MgSO_4$) extract was evaporated to give the title compound as a white solid (2.33 g).

$^1$H NMR DMSO-d6: δ 12.98 (1H, s), 7.16 (1H, dd), 6.83 (1H, dd), 6.27 (1H, s), 4.92 (2H, s), 2.32—2.32 (6H, m) MS: APCI−[M−H] 220 vi) 3-[(4-Chlorophenyl)thio]-5-fluoro-2,4-dimethyl-1H-indole-1-acetic acid

A stirred solution of the product from step v) (221 mg) and iodine (508 mg) in DMF (2 ml) was treated with a solution of 4-chlorothiophenol (288 mg) and stirred overnight. The solution was purified by reversed phase preparative HPLC to give the title compound (50 mg).

MS: APCI−[M−H] 362 $^1$H NMR DMSO-d6: δ 7.30–7.25 (3H, m), 6.97–6.89 (3H, m), 4.74 (2H, s), 2.44 (3H, d), 2.36 (3H, s)

EXAMPLE 44

3-[(4-Cyanophenyl)thio]-5-fluoro-2,4-dimethyl-1H-indole-1-acetic acid

The title compound was prepared from the product of example 49), step v) (221 mg), iodine (508 mg) and 4-thiobenzonitrile (270 mg) by the method of example 49), step vi).

MS: APCI−[M−H] 353 $^1$H NMR DMSO-d6: δ 7.68–7.63 (2H, m), 7.33–7.29 (1H, m), 7.12–7.08 (2H, m), 6.98–6.92 (1H, m), 4.78 (2H, s), 2.40 (3H, d), 2.35 (3H, s)

EXAMPLE 45

3-[(2-Chlorophenyl)thio]-5-fluoro-2,4-dimethyl-1H-indol-1-acetic acid

The title compound was prepared from the product of example 49), step v) (221 mg), iodine (508 mg) and 2-chlorothiophenol (289 mg) by the method of example 49), step vi).

MS: APCI−[M−H] 362 $^1$H NMR DMSO-d6: δ 7.45–7.42 (1H, m), 7.25–7.21 (1H, m), 7.13–7.06 (2H, m), 6.94–6.87 (1H, m), 6.53–6.50 (1H, m), 4.53 (2H, s), 2.39 (3H, d), 2.33 (3H, s)

EXAMPLE 46

5-Fluoro-3-[(2-methoxyphenyl)thio]-2,4-dimethyl-1H-indole-1-acetic acid

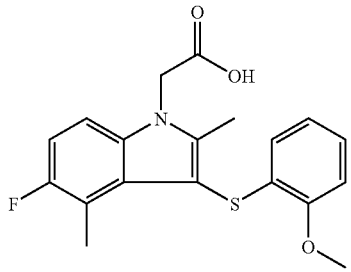

The title compound was prepared from the product of example 49), step v) (221 mg), iodine (508 mg) and 2-methoxythiophenol (280 mg) by the method of example 49), step vi).

MS: APCI–[M–H] 358 $^1$H NMR DMSO-d6: δ 7.39–7.34 (1H, m), 7.08–6.93 (3H, m), 6.74–6.69 (1H, m), 6.33 (1H, dd), 5.09 (2H, s), 3.89 (3H, s), 2.40 (3H, d), 2.34 (3H, s)

EXAMPLE 47

5-Fluoro-3-[(2-ethylphenyl)thio]-2,4-dimethyl-1H-indole-1-acetic acid

The title compound was prepared from the product of example 49), step v) (221 mg), iodine (508 mg) and 2-ethylthiophenol (276 mg) by the method of example 49), step vi).

MS: APCI–[M–H] 356 $^1$H NMR DMSO-d6: δ 7.28–7.23 (1H, m), 7.18 (1H, dd), 7.03–6.87 (3H, m), 6.47 (1H, dd), 4.71 (2H, s), 2.80 (2H, q), 2.40 (3H, d), 2.35 (3H, s), 1.29 (3H, t)

EXAMPLE 48

5-Fluoro-2,4-dimethyl-3-[[2-(1-methylethyl)phenyl]thio]-1H-indole-1-acetic acid

The title compound was prepared from the product of example 49), step v) (221 mg), iodine (508 mg) and 2-isopropylthiophenol (304 mg) by the method of example 49), step vi).

MS: APCI–[M–H] 370 $^1$H NMR DMSO-d6: δ 7.29–7.25 (2H, m), 7.03 (1H, td), 6.95–6.88 (2H, m), 6.47 (1H, dd), 4.78 (2H, s), 3.44 (1H, quintet), 2.40 (3H, d), 2.35 (3H, s), 1.30 (6H, d).

EXAMPLE 49

5-fluoro-2,4-dimethyl-3-[[2-(trifluoromethyl)phenyl]thio]-1H-indole-1-acetic acid The title compound was prepared from the product of example 49), step v) (221 mg), iodine (508 mg) and 2-trifluoromethylthiophenol (356 mg) by the method of example 49), step vi).

MS: APCI–[M–H] 396 $^1$H NMR DMSO-d6: δ 7.70 (1H, d), 7.38 (1H, t), 7.27–7.23 (2H, m), 6.91 (1H, t), 6.76 (1H, d), 4.57 (2H, s), 2.38 (3H, d) and 2.35 (3H, s).

EXAMPLE 50

2,5-dimethyl-4-(methylsulfonyl)-3-[(4-phenyl-2-thiazolyl)thio]-1H-indole-1-acetic acid i) 2,5-dimethyl-4-methylsulfonyl)-3-(methylthio)-1H-indole The title compound was made by the method of example 43 step i) using 4-methyl-3-(methylsulfonyl)-benzenamine.

$^1$H NMR DMSO-d6: δ 11.94 (1H, s), 7.49 (1H, d), 7.01 (1H, d), 3.51 (3H, s), 2.69 (3H, s), 2.55 (3H, s), 2.19 (3H, d)

b) 2,5-dimethyl-4-(methylsulfonyl)-1H-indole

A solution of the product from part a) (1.00 g) and thiosalicylic acid (1.15 g) in trifluoroacetic acid (20 ml) was stirred at 60° C. for 2 hours and then concentrated in vacuo. The residue was taken up in methylene chloride, washed with 1N aqueous sodium hydroxide solution followed by water, dried (MgSO$_4$) and evaporated to give the title compound (0.47 g).

$^1$H NMR DMSO-d6: δ 11.36 (1H, s), 7.46 (1H, d), 6.99 (1H, d), 6.64 (1H, d), 3.33 (3H, s), 3.10 (3H, s), 2.66 (3H, s)

c) 2,5-dimethyl-4-(methylsulfonyl)-3-[(phenyl-2-thiazolyl)thio]-1H-indole-1-acetic acid A stirred solution of the product from step b) (200 mg) and iodine (210 mg) in DMF (2 ml) was treated with 2-thiazolethiol, 4-phenyl- (300 mg) and stirred for 1 hour. The solution was treated with 60% sodium hydride (4.0 molar equivalents) and stirred overnight. Methyl bromoacetate (0.30 g) was added followed after 30 minutes stirring by water (2 ml) tetrahydrofuran (2 ml) and lithium hydroxide (0.20 g). After stirring a further 30 minutes, the reaction mixture was acidified (2M HCl, 5 ml) and extracted into ethyl acetate (3×10 ml). The combined organics were washed with saturated brine (3×10 ml), dried (MgSO$_4$) and evaporated. The residue was purified by reversed phase preparative HPLC to give the title compound (172 mg).

MS: APCI–[M–H] 471 $^1$H NMR DMSO-d6: δ 7.94–0.69 (4H, m), 7.49–7.24 (3H, m), 7.19 (1H, d), 5.05 (2H, s), 3.57 (3H, s), 3.34 (3H, s), 2.80 (3H, s).

EXAMPLE 51

3-[(3-chlorophenyl)thio]-2,5-dimethyl-4-(methylsulfonyl)-1H-indole-1-acetic acid The title compound was made by the procedure of example 50 step iii) using the product from step ii) (200 mg) and 3-chlorobenzenethiol (0.3 g).

The compound was purified by reversed phase preparative HPLC to give the title compound (40 mg).

MS: APCI–[M–H] 422 $^1$H NMR DMSO-d6: δ 7.83–7.69 (1H, m), 7.26–6.97 (3H, m), 6.88–6.73 (2H, m), 5.01 (2H, d), 3.57 (3H, s), 3.32 (3H, s), 2.69 (3H, s)

EXAMPLE 52

3-[(2-chlorophenyl)thio]-2,5-dimethyl-4-(methylsulfonyl)-1H-indole-1-acetic acid The title compound (55 mg) was prepared by the method of example 57 step iii) using the product from step ii) (200 mg) and 2-chlorobenzenethiol (0.3 g).

MS: APCI−[M−H] 422 $^1$H NMR DMSO-d6: δ 7.76 (1H, d), 7.39 (1H, m), 7.21–6.95 (3H, m), 6.34 (1H, m), 4.93 (2H, s), 3.64 (3H, s), 3.29 (3H, s), 2.69 (3H, s)

EXAMPLE 53

3-[(4-chlorophenyl)thio]-5-(methoxycarbonyl)-2-methyl-1H-indole-1-acetic acid

(i) 3-[(4-chlorophenyl)thio]-2-methyl-1H-indole-5-carboxylic acid

To a solution of the product from part 27 (i) (2 g) in ethanol (20 ml) was added 12.5M solution of sodium hydroxide (5 ml). The mixture was heated to reflux for 4 days. After cooling the mixture was poured into water and the pH adjusted to 2 using concentrated HCl (aq). The solid which precipitated was isolated by filtration and then recrystallised from boiling methanol to give the sub-title compound (2 g).

$^1$H NMR DMSO-d6: δ 12.51 (1H, s), 12.05 (1H, s), 7.96 (1H, d), 7.75 (1H, dd), 7.46 (1H, dd), 7.27 (2H, dd), 6.97 (2H, dd), 2.47 (3H, s)

(ii) 3-[(4-chlorophenyl)thio]-2-methyl-1H-indole-5-carboxylic acid, methyl ester To a solution/suspension of the product from part (i) (1 g) in methanol (50 ml) was added trimethylsilylchloride (12.6 ml). After stirring at room temperture overnight the mixture was concentrated in vacuo to give sub-title compound in quantitative yield.

$^1$H NMR DMSO-d6: δ 12.12 (1H, s), 7.97 (1H, d), 7.77 (1H, dd), 7.49 (1H, dd), 7.27 (2H, dt), 6.97 (2H, dt), 3.80 (3H, s), 2.47 (3H, s)

(iii) 3-[(4-chlorophenyl)thio]-5-(methoxycarbonyl)-2-methyl-1H-indole-1-acetic acid, 1,1-dimethylethyl ester The sub-title compound was prepared by the method of example 11 part (ii) using the product of part (ii) and t-butylbromoacetate. The product was purified using flash column chromatography (14% EtOAc/hexane as eluent).

$^1$H NMR DMSO-d6: δ 8.01 (1H, d), 7.82 (1H, dd), 7.67 (1H, d), 7.28 (2H, m), 6.97 (2H, dt), 5.20 (2H, s), 3.81 (3H, s), 2.44 (3H, s), 1.42 (9H, s)

(iv) 3-[(4-chlorophenyl)thio]-5-(methoxycarbonyl)-2-methyl-1H-indole-1-acetic acid The title compound was prepared by the method of example (22) part (iii) using the product from part (iii).

$^1$H NMR DMSO-d6: δ 13.28 (1H, s), 8.01 (1H, d), 7.81 (1H, dd), 7.68 (1H, d), 7.28 (2H, d), 6.98 (2H, d), 5.20 (2H, s), 3.82 (3H, s), 2.45 (3H, s). MS: APCI−[M−H] 388 M.pt 221–223° C.

EXAMPLE 54

5-carboxy-3-[(4-chlorophenyl)thio]-2-methyl-1H-indole-1-acetic acid

(i) 5-carboxy-3-[(4-chlorophenyl)thio]-2-methyl-1H-indole-1-acetic acid

A suspension of the product from example 53 (0.5 g) in 1M sodium hydroxide(aq) (3 ml) was heated in a sealed tube at 100° C. using a microwave for 10 minutes. The mixture was poured into water and the pH adjusted to 2 using 2M HCl(aq). The solid which precipitated was isolated by filtration, dried overnight under vacuum at 50° C. to give the title compound (0.1 g).

$^1$H NMR DMSO-d6: δ 7.99 (1H, d), 7.79 (1H, dd), 7.64 (1H, d), 7.28 (2H, dd), 6.99 (2H, dt), 5.19 (2H, s), 2.45 (3H, s) MS: APCI−[M−H] 374 M.pt dec>302° C.

EXAMPLE 55

3-[(4-chlorophenyl)thio]-2-methyl-4-nitro-1H-indole-1-acetic acid i) 3-[(4-chlorophenyl)thio]-2-methyl-4-nitro-1H-indole

To a stirred solution of 3-nitroaniline (8 g) in THF (700 ml) cooled to −78° C. was added t-butyl hypochlorite (6.3 g) dropwise over 5 minutes. The reaction was allowed to warm to −65° C. over 20 minutes before 1-[4-chlorophenyl)thio]-2-propanone (11.6 g) was added as a solution in tetrahydrofuran (20 ml). After 2 hours triethylamine (8.1 ml) was added and the reaction allowed to warm to room temperature. 2M HCl (aq) was added to the reaction mixture before concentration in vacuo. The residue was slurried in methanol and the solid which precipitated isolated by filtration to give the sub-title compound (5.8 g).

$^1$H NMR DMSO-d6: δ 12.55 (s, 1H), 7.76 (dd, 1H), 7.63 (dd, 1H), 7.31–7.22 (m, 3H), 6.91 (dd, 2H), 2.47 (s, 3H)

ii) 3-[(4-chlorophenyl)thio]-2-methyl-4-nitro-1H-indole-acetic acid, ethyl ester To a stirred suspension of sodium hydride, 60% dispersion in mineral oil, (0.85 g) in THF (100 ml) was added the product from part (i) (5.6 g) as a solution in THF (50 ml). After stirring at room temperature for 30 minutes ethyl bromoacetate (2.3 ml) was added dropwise over 10 minutes. After 2 hours the reaction was concentrated in vacuo, the residue dissolved in ethyl acetate, washed with water, brine, dried (MgSO$_4$) and concentrated in vacuo. Recrystallisation from boiling ethanol gave the sub-title compound (5 g).

$^1$H NMR DMSO-d6: δ 7.97 (dd, 1H), 7.65 (dd, 1H), 7.35 (t, 1H), 7.26 (dt, 2H), 6.92 (dt, 2H), 5.40 (s, 2H), 4.19 (q, 2H), 2.45 (s, 3H), 1.22 (t, 3H).

iii) 3-[(4-chlorophenyl)thio]-2-methyl-4-nitro-1H-indole-acetic acid

To a solution of the product from part (ii) (0.1 g) in THF (5 ml) was added a 1M solution of NaOH (aq) (0.25 ml). The reaction was stirred overnight at room temperature. The reaction mixture was concentrated in vacuo and the residue dissolved/suspended in water. The pH was adjusted to 2 using dilute HCl (aq) and the solid which precipitated isolated by filtration, dried under vaccum at 50° C. to give the title compound (0.07 g).

¹H NMR DMSO-d6: δ 13.37 (s, 1H), 7.97 (d, 1H), 7.64 (d, 1H), 7.34 (t, 1H), 7.25 (dt, 2H), 6.92 (dt, 2H), 5.28 (s, 2H), 2.45 (s, 3H). MS: APCI–[M–H] 375 M.pt. dec>198° C.

EXAMPLE 56

4-amino-3-[(4-chlorophenyl)thio]-2-methyl-1H-indole-1-acetic acid i) 4-amino-3-[(4-chlorophenyl)thio]-2-methyl-1H-indole-1-acetic acid, ethyl ester A suspension of the product from example 55 part (ii) (2.25 g) in ethanol (170 ml) was stirred in the presence of 5% Pt/C (0.5 g) under 2 bar pressure of $H_2$. After stirring overnight the catalyst was removed by filtration and the filtrates concentrated in vacuo. Purification by flash column chromatography (14% EtOAc/hexane as eluent) gave the sub-title compound (1.4 g).

¹H NMR (DMSO) δ 7.30 (dd, 2H), 7.00 (dt, 2H), 6.85 (t, 1H), 6.68 (dd, 1H), 6.23 (dd, 1H), 5.33 (s, 2H), 5.09 (s, 2H), 4.16 (q, 2H), 2.33 (s, 3H), 1.21 (t, 3H).

3-[(4-chlorophenyl)thio]4-(ethylamino)-2-methyl-1H-indole-1-acetic acid, ethyl ester was also isolated as a by product from the reaction (0.33 g).

¹H NMR DMSO-d6: δ 7.32 (dd, 2H), 7.01 (dd, 2H), 6.95 (t, 1H), 6.73 (d, 1H), 6.16 (d, 1H), 5.70 (t, 1H), 5.11 (s, 2H), 4.16 (q, 2H), 3.05 (dt, 2H), 2.34 (s, 3H), 1.21 (t, 3H), 1.02 (t, 3H).

ii) 4-amino-3-[(4-chlorophenyl)thio]-2-methyl-1H-indole-1-acetic acid

Title compound was prepared using the method of example 1 part (iii) (0.03 g).

¹H NMR (DMSO) δ 7.29 (dt, 2H), 7.01 (dt, 2H), 6.88 (t, 1H), 6.76 (d, 1H), 6.30 (d,1H), 4.99 (s, 2H), 2.33 (s, 3H). MS: APCI–[M–H] 345 M.pt. dec>235° C.

EXAMPLE 57

3-[(4-chlorophenyl)thio]-4-(ethylamino)-2-methyl-1H-indole-1-acetic acid

The compound was prepared using the method of example 55 part (ii) using the by product from example 2 part (i). Purification by reverse phase preparative HPLC.

¹H NMR DMSO-d6: δ 7.29 (dt, 2H), 7.02 (m, 2H), 6.88 (t, 1H) 6.64 (d, 1H), 6.11 (d, 1H), 5.66 (t, 1H), 4.51 (s, 2H), 3.04 (dt, 2H), 2.31 (s, 3H), 1.01 (t, 3H). MS: APCI+[M+H] 375.

EXAMPLE 58

3-[(4-chlorophenyl)thio]-4-iodo-2-methyl-1H-indole-1-acetic acid (i) 3-[(4-chlorophenyl)thio]-4-iodo-2-methyl-1H-indole The sub-title compound was prepared by the method of example 27 part (i) using 3-iodoaniline. The product was purified using flash column chromatography (14% EtOAc/hexane as eluent).

¹H NMR DMSO-d6: δ 11.99 (1H, s), 7.50 (1H, dd), 7.44 (1H, dd), 7.26 (2H, m), 6.92–6.84 (3H, m), 2.43 (3H, s)

(ii) 3-[(4-chlorophenyl)thio]-4-iodo-2-methyl-1H-indole-1-acetic acid

The sub-title compound was prepared by the method of example 11 parts (ii) and part (iii) using the product from part (i).

¹H NMR DMSO-d6: δ 7.52 (2H, d), 7.25 (2H, dt), 6.93–6.86 (3H, m), 4.86 (2H, s), 2.40 (3H, s) MS: APCI–[M–H] 456

EXAMPLE 59

3-[(4-chlorophenyl)thio]-2-methyl-4-phenyl-1H-indole-1-acetic acid i) 3-[(4-chlorophenyl)thio]-2-methyl-4-phenyl-1H-indole-1-acetic acid, 1,1-dimethylethyl ester To a solution of the product of example 22 part (ii) (0.5 g) in ethanol (0.8 ml) and toluene (3 ml) was added 2M sodium carbonate solution in water (1.4 ml), phenylboronic acid (0.131 g) and tetrakis(triphenylphosphine)palladium(0) (1.2 g). The reaction was heated to reflux for 2 hours, cooled and concentrated in vacuo. The residue was purified by flash column chromatography to give the sub-title compound (0.4 g). This was used in step (ii) without further characterisation.

ii) 3-[(4-chlorophenyl)thio]-2-methyl-4-phenyl-1H-indole-1-acetic acid

To a solution of the product from part (i) (0.4 g) in dichloromethane (10 ml) was added trifluoroacetic acid (2 ml), the reaction was stirred at room temperature overnight. The reaction was concentrated in vacuo and the residue dissolved/suspended in water. The pH was adjusted to 2 using 2M HCl(aq) and the solid which precipitated was isolated by filtration. This was purifed using reverse phase preparative HPLC (MeCN/NH3(aq) as eluent) to give a solid. The solid was suspended in water and the pH was adjusted to 2 using 2M HCl(aq), the solid was isolated by filtration, triturated with hexane and dried overnight at 40° C. under vaccum to give the title compound (0.15 g).

¹H NMR DMSO-d6: δ 7.55 (d, 1H), 7.26–7.07 (m, 8H), 6.87 (d, 1H), 6.56 (m, 2H), 5.18 (s, 2H), 2.40 (s, 3H). MS: APCI+[M+H] 408

Pharmacological Data

Ligand Binding Assay

[³H]PGD$_2$ was purchased from Perkin Elmer Life Sciences with a specific activity of 100–210 Ci/mmol. All other chemicals were of analytical grade.

HEK cells expressing rhCRTh2/Gα16 were routinely maintained in DMEM containing 10% Foetal Bovine Serum (HyClone), 1 mg/ml geneticin, 2 mM L-glutamine and 1% non-essential amino acids. For the preparation of membranes, the adherent transfected HEK cells were grown to confluence in two layer tissue culture factories (Fisher, catalogue number TKT-170-070E). Maximal levels of receptor expression were induced by addition of 500 mM sodium butyrate for the last 18 hours of culture. The adherent cells were washed once with phosphate buffered saline (PBS, 50 ml per cell factory) and detached by the addition of 50 ml per cell factory of ice-cold membrane homogenisation buffer [20 mM HEPES (pH 7.4), 0.1 mM dithiothreitol, 1 mM EDTA, 0.1 mM phenyl methyl sulphonyl fluoride and 100 µg/ml bacitracin]. Cells were pelleted by centrifugation at 220×g for 10 minutes at 4° C., re-suspended in half the original volume of fresh membrane homogenisation buffer and disrupted using a Polytron homogeniser for 2×20 second bursts keeping the tube in ice at all times. Unbroken cells were removed by centrifugation at 220×g for 10 minutes at 4° C. and the membrane fraction pelleted by centrifugation at 90000×g for 30 minutes at 4° C. The final pellet was re-suspended in 4 ml of membrane homogenisation buffer per cell factory used and the protein content determined. Membranes were stored at −80° C. in suitable aliquots.

All assays were performed in Corning clear bottomed, white 96-well NBS plates (Fisher). Prior to assay, the HEK cells membranes containing CRTh2 were coated onto SPA PVT WGA beads (Amersham). For coating membranes were incubated with beads at typically 25 μg membrane protein per mg beads at 4° C. with constant agitation overnight. (The optimum coating concentrations were determined for each batch of membranes) The beads were pelleted by centrifugation (800×g for 7 minutes at 4° C.), washed once with assay buffer (50 mM HEPES pH 7.4 containing 5 mM magnesium chloride) and finally re-suspended in assay buffer at a bead concentration of 10 mg/ml.

Each assay contained 20 μl of 6.25 nM [$^3$H]PGD$_2$, 20 μl membrane saturated SPA beads both in assay buffer and 10 μl of compound solution or 13,14-dihydro-15-keto prostaglandin D$_2$ (DK-PGD$_2$, for determination of non-specific binding, Cayman chemical company). Compounds and DK-PGD$_2$ were dissolved in DMSO and diluted in the same solvent to 100× the required final concentration. Assay buffer was added to give a final concentration of 10% DMSO (compounds were now at 10× the required final concentration) and this was the solution added to the assay plate. The assay plate was incubated at room temperature for 2 hours and counted on a Wallac Microbeta liquid scintillation counter (1 minute per well).

Compounds of formula (I) have an IC$_{50}$ value of less than (<) 10 μM.

Specifically, example 23 has a pIC$_{50}$=6.05, example 50 has a pIC$_{50}$=7.2 and example 29 has a pIC$_{50}$=8.35.

The invention claimed is:

1. A compound of formula (I) or a pharmaceutically acceptable salt thereof:

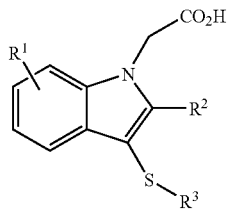

(I)

in which

R$^1$ is hydrogen, halogen, CN, nitro, SO$_2$R$^4$, OH, OR$^4$, S(O)xR$^4$, SO$_2$NR$^5$R$^6$, CONR$^5$R$^6$, NR$^5$R$^6$, aryl (optionally substituted by chlorine or fluorine), C$_2$–C$_6$ alkenyl, C$_2$–C$_6$ alkynyl or C$_{1-6}$ alkyl, the latter three groups being optionally substituted by one or more substituents independently selected from halogen, OR$^8$ and NR$^5$R$^6$, S(O)$_x$R$^7$ where x is 0,1 or 2;

R$^2$ is hydrogen, halogen, CN, SO$_2$R$^4$ or CONR$^5$R$^6$, CH$_2$OH, CH$_2$OR$^4$ or C$_{1-7}$alkyl, the latter group being optionally substituted by one or more substituents independently selected from halogen atoms, OR$^8$ and NR$^5$R$^6$, S(O)$_x$R$^7$ where x is 0, 1 or 2;

R$^3$ is aryl or heteroaryl each of which is optionally substituted by one or more substituents independently selected from hydrogen, halogen, CN, OH, SO$_2$R$^4$, OR$^4$, SR$^4$, SOR$^4$, SO$_2$NR$^5$R$^6$, CONR$^5$R$^6$, NR$^5$R$^6$, NHCOR$^4$, NHSO$_2$R$^4$, NHCO$_2$R$^4$, NR$^7$SO$_2$R$^4$, NR$^7$CO$_2$R$^4$, C$_2$–C$_6$ alkenyl, C$_2$–C$_6$ alkynyl, C$_{1-6}$ alkyl, the latter three groups being optionally substituted by one or more substituents independently selected from halogen atoms, OR$^8$ and NR$^5$R$^6$, S(O)$_x$R$^7$ where x=0,1 or 2;

R$^4$ represents aryl, heteroaryl, or C$_{1-6}$alkyl all of which may be optionally substituted by one or more substituents independently selected from halogen atoms, aryl, heteroaryl, OR$^{10}$, OH, NR$^{11}$R$^{12}$, S(O)$_x$R$^{13}$ (where x=0,1 or 2), CONR$^{14}$R$^{15}$, NR$^{14}$COR$^{15}$, SO$_2$NR$^{14}$R$^{15}$, NR$^{14}$SO$_2$R$^{15}$, CN, nitro;

R$^5$ and R$^6$ independently represent a hydrogen atom, a C$_{1-6}$alkyl group, or an aryl, or a heteroaryl, the latter three of which may be optionally substituted by one or more substituents independently selected from halogen atoms, aryl, OR$^8$ and NR$^{14}$R$^{15}$, CONR$^{14}$R$^{15}$, NR$^{14}$COR$^{15}$, SO$_2$NR$^{14}$R$^{15}$, NR$^{14}$SO$_2$R$^{15}$; CN, nitro or R$^5$ and R$^6$ together with the nitrogen atom to which they are attached can form a 3–8 membered saturated heterocylic ring optionally containing one or more atoms selected from O, S(O)$_x$ where x=0,1 or 2, NR$^{16}$, and itself optionally substituted by C$_{1-3}$ alkyl;

R$^7$ and R$^{13}$ independently represent a C$_1$–C$_6$, alkyl, an aryl or a heteroaryl group, all of which may be optionally substituted by halogen atoms;

R$^8$ represents a hydrogen atom, C(O)R$^9$, C$_1$–C$_6$ alkyl (optionally substituted by halogen atoms or aryl) an aryl or a heteroaryl group (optionally substituted by halogen);

each of R$^9$ R$^{10}$, R$^{11}$, R$^{12}$, R$^{14}$, R$^{15}$, independently represents a hydrogen atom, C$_1$–C$_6$ alkyl, an aryl or a heteroaryl group; and R$^{16}$ is hydrogen, C$_{1-4}$ alkyl, —COC$_1$–C$_4$ alkyl, COYC$_1$–C$_4$alkyl where Y is O or NR$^7$, each of R$^9$ R$^{10}$, R$^{11}$, R$^{12}$, R$^{14}$, R$^{15}$, independently represents a hydrogen atom, C$_1$–C$_6$ alkyl, an aryl or a heteroaryl group (all of which may be optionally substituted by halogen atoms); and R$^{16}$ is hydrogen, C$_{1-4}$ alkyl, —COC$_1$–C$_4$ alkyl, COYC$_1$–C$_4$alkyl where Y is O or NR$^7$, In the context of the present specification, unless otherwise indicated, an alkyl or alkenyl group or an alkyl or alkenyl moiety in a substituent group may be linear, branched or cyclic.

2. A compound according to claim 1 in which R$^1$ is aryl, hydrogen, methyl, chloro, fluoro, nitrile, nitro, bromo, iodo, SO$_2$Me, SO$_2$Et, NR$^4$R$^5$, SO$_2$N-alkyl$_2$.

3. A compound according to claim 1 in which R$^2$ is C$_{1-6}$alkyl.

4. A compound according to claim 3 in which R$^3$ is quinolyl, phenyl or thiazole, substituted by one or more fluorine, chlorine, methyl, ethyl, isopropyl, methoxy, SO$_2$Me, trifluoromethyl or aryl groups.

5. A compound according to claim 1 selected from:
3-[(4-chlorophenyl)thio]-2,5-dimethyl-1H-indol-1-acetic acid;
3-[(2-chloro-4-fluorophenyl)thio]-2,5-dimethyl-1H-indol-1-acetic acid;
3-[(3-chloro-4-fluorophenyl)thio]-2,5-dimethyl-1H-indol-1-acetic acid;
3-[(2-methoxyphenyl)thio]-2,5-dimethyl-1H-indol-1-acetic acid;

3-[(3-fluorophenyl)thio]-2,5-dimethyl-1H-indol-1-acetic acid;
3-[(4-ethylphenyl)thio]-2,5-dimethyl-1H-indol-1-acetic acid;
3-[(2-chlorophenyl)thio]-2,5-dimethyl-1H-indol-1-acetic acid;
3-[(2,5-dichlorophenyl)thio]-2,5-dimethyl-1H-indol-1-acetic acid;
3-[(4-fluorophenyl)thio]-2,5-dimethyl-1H-indol-1-acetic acid;
3-[(4-chloro-2-methylphenyl)thio]-2,5-dimethyl-1H-indol-1-acetic acid;
3-[(4-chlorophenyl)thio]-4-cyano-2,5-dimethyl-1H-indole-1-acetic acid;
5-chloro-3-[(4-chlorophenyl)thio]-6-cyano-2-methyl-1H-indole-1-acetic acid;
3-[(4-chlorophenyl)thio]-4-(ethylsulfonyl)-7-methoxy-2-methyl-1H-indole-1-acetic acid;
3-[(4-chlorophenyl)thio]-4-[(diethylamino)sulfonyl]-7-methoxy-2-methyl-1H-indole-1-acetic acid;
4-chloro-3-[(4-chlorophenyl)thio]-2-methyl-1H-indole-1-acetic acid;
5-chloro-3-[(4-chlorophenyl)thio]-2-methyl-1H-indole-1-acetic acid;
6-chloro-3-[(4-chlorophenyl)thio]-2-methyl-1H-indole-1-acetic acid;
7-chloro-3-[(4-chlorophenyl)thio]-2-methyl-1H-indole-1-acetic acid;
3-[(4-chlorophenyl)thio]-2-methyl-5-(methylsulfonyl)-1H-indole-1-acetic acid;
2-methyl-3-[(4-methylphenyl)thio]-6-(methylsulfonyl)-1H-indole-1-acetic acid;
4-bromo-3-[(4-chlorophenyl)thio]-2-methyl-1H-indole-1-acetic acid;
3-[(4-chlorophenyl)thio]-4-[4-[(1,1-dimethylethoxy)carbonyl]-1-piperazinyl]-2-methyl-1H-indole-1-acetic acid;
3-[(4-chlorophenyl)thio]-2-methyl-4-(1-piperazinyl)-1H-indole-1-acetic acid;
5-bromo-3-[(4-chlorophenyl)thio]-2-methyl-1H-indole-1-acetic acid;
3-[(4-chlorophenyl)thio]-2-methyl-5-phenyl-1H-indole-1-acetic acid;
3-[(4-chlorophenyl)thio]-5-cyano-2-methyl-1H-indole-1-acetic acid;
3-[(4-cyanophenyl)thio]-2,5-dimethyl-1H-indol-1-acetic acid,
3-[(3-methoxyphenyl)thio]-2,5-dimethyl-1H-indole-1-acetic acid;
3-[(4-methoxyphenyl)thio]-2,5-dimethyl-1H-indole-1-acetic acid,
3-[(3-ethylphenyl)thio]-2,5-dimethyl-1H-indole-1-acetic acid
2,5-dimethyl-3-[(2-methylphenyl)thio]-1H-indole-1-acetic acid;
3-[(3-chlorophenyl)thio]-2,5-dimethyl-1H-indole-1-acetic acid,
3-[(2-Fluorophenyl)thio]-2,5-dimethyl-1H-indole-1-acetic acid,
3-[(2,6-Dichlorophenyl)thio]-2,5-dimethyl-1H-indole-1-acetic acid;
3-(1H-Imidazol-2-ylthio)-2,5-dimethyl-1H-indole-1-acetic acid,
2,5-Dimethyl-3-(1H-1,2,4-triazol-3-ylthio)-1H-indole-1-acetic acid;
2,5-Dimethyl-3-[(4-methyl-4H-1,2,4-triazol-3-yl)thio]-1H-indole-1-acetic acid;
2,5-Dimethyl-3-[(4-methyl-2-oxazolyl)thio]-1H-indole-1-acetic acid;
2,5-Dimethyl-3-[(1-methyl-1H-imidazol-2-yl)thio]-1H-indole-1-acetic acid;
2,5-Dimethyl-3-[[4-(methylsulfonyl)phenyl]thio]-1H-indole-1-acetic acid,
2,5-Dimethyl-3-(8-quinolinylthio)-1H-indole-1-acetic acid,
3-[(4-Chlorophenyl)thio]-5-fluoro-2,4-dimethyl-1H-indole-1-acetic acid;
3-[(4-Cyanophenyl)thio]-5-fluoro-2,4-dimethyl-1H-indole-1-acetic acid;
3-[(2-Chlorophenyl)thio]-5-fluoro-2,4-dimethyl-1H-indole-1-acetic acid;
5-Fluoro-3-[(2-methoxyphenyl)thio]-2,4-dimethyl-1H-indole-1-acetic acid;
5-Fluoro-3-[(2-ethylphenyl)thio]-2,4-dimethyl-1H-indole-1-acetic acid;
5-Fluoro-2,4-dimethyl-3-[[2-(1-methylethyl)phenyl]thio]-1H-indole-1-acetic acid;
5-fluoro-2,4-dimethyl-3-[[2-(trifluoromethyl)phenyl]thio]-1H-indole-1-acetic acid;
2,5-dimethyl-4-(methylsulfonyl)-3-[(4-phenyl-2-thiazolyl)thio]-1H-indole-1-acetic acid;
3-[(3-chlorophenyl)thio]-2,5-dimethyl-4-(methylsulfonyl)-1H-indole-1-acetic acid;
3-[(2-chlorophenyl)thio]-2,5-dimethyl-4-(methylsulfonyl)-1H-indole-1-acetic acid;
3-[(4-chlorophenyl)thio]-5-(methoxycarbonyl)-2-methyl-1H-indole-1-acetic acid;
5-carboxy-3-[(4-chlorophenyl)thio]-2-methyl-1H-indole-1-acetic acid;
3-[(4-chlorophenyl)thio]-2-methyl-4-nitro-1H-indole-1-acetic acid;
4-amino-3-[(4-chlorophenyl)thio]-2-methyl-1H-indole-1-acetic acid;
3-[(4-chlorophenyl)thio]-4-(ethylamino)-2-methyl-1H-indole-1-acetic acid;
3-[(4-chlorophenyl)thio]-4-iodo-2-methyl-1H-indole-1-acetic acid;
3-[(4-chlorophenyl)thio]-2-methyl-4-phenyl-1H-indole-1-acetic acid;

and pharmaceutically acceptable salts thereof.

6. A method of treating asthma which comprises administering to a patient a therapeutically effective amount of a compound of formula (I), or a pharmaceutically acceptable salt as defined in claim 1.

7. A process for the preparation of a compound of formula (I) which comprises reaction of a compound of formula (II):

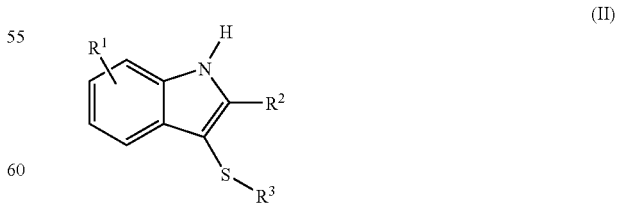

(II)

in which $R^1$, $R^2$ and $R^3$ are as defined in formula (I) or are protected derivatives thereof, with a compound of formula (A):

L-CH$_2$CO$_2$R$^{17}$ (A)

where $R^{17}$ is an ester forming group and L is a leaving group in the presence of a base, and optionally thereafter in any order:
removing any protecting group
hydrolysing the ester group $R^{17}$ to the corresponding acid forming a pharmaceutically acceptable salt.

* * * * *